US006852320B2

(12) United States Patent  
Blumberg

(10) Patent No.: US 6,852,320 B2
(45) Date of Patent: Feb. 8, 2005

(54) T CELL INHIBITORY RECEPTOR COMPOSITIONS AND USES THEREOF

(75) Inventor: Richard S. Blumberg, Chestnut Hill, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 141 days.

(21) Appl. No.: 09/884,196

(22) Filed: Jun. 19, 2001

(65) Prior Publication Data

US 2002/0028203 A1 Mar. 7, 2002

Related U.S. Application Data

(62) Division of application No. 09/293,504, filed on Apr. 15, 1999.
(60) Provisional application No. 60/081,895, filed on Apr. 15, 1998.

(51) Int. Cl.⁷ ...................... A61K 39/395; A61K 38/16; C07K 16/28
(52) U.S. Cl. ................ 424/133.1; 424/134.1; 424/154.1; 514/8; 530/387.1; 530/387.3; 530/388.2; 530/388.73; 530/388.85; 530/395
(58) Field of Search ................ 424/133.1, 134.1, 424/154.1; 514/8; 530/387.1, 387.3, 388.3, 388.73, 388.85, 395, 386.2

(56) References Cited

U.S. PATENT DOCUMENTS 5,288,854 A  2/1994  Diamond et al.
5,688,690 A  11/1997 Valiante et al.

FOREIGN PATENT DOCUMENTS

WO   WO 99/52552 A1   10/1999
WO   WO 01/13937 A1   3/2001

OTHER PUBLICATIONS

Ebert, *Clin. Exp. Immunol.*, 82(1):81–85, 1990.
Lundqvist et al., *J. Immunol.*, 157:1926–1934, 1996.
Balk et al., *Science*, 253:1411–1415, 1991.
Jarry et al., *Eur. J. Immunol.*, 20:1097–1103, 1990.
Blumberg et al., *J. Immunol.*, 150:5144–5153, 1993.
Van Kerckhove et al., *J. Exp. Med.*, 175:57–63, 1992.
Chowers et al., *J. Exp. Med.*, 180:183–190, 1994.
Gelfanov et al., *J. Immunol*, 155:76–82, 1995.
Gramzinski et al., *Int. Immunol.* 5:145–153, 1993.
Russell et al., *J. Immunol.*, 157:3366–3374, 1996.
Anumanthan et al., *J.Immunol.*, 161:2780–2790, 1998.

Parker et al., *Proc. Natl. Acad. Sci.*, 89:1924–1928, 1992.
Lanier et al., *Sem. in Immunol.*, 7:75–82, 1995.
Walunas et al., *J. Exp. Med.*, 183:2541–2550, 1996.
Krummel et al., *J. Exp. Med.* 183:2533–2540, 1996.
Vely et al., *J. Immunol.*, 159:2075–2077, 1997.
Cambier, *Proc. Natl. Acad. Sci.*, 94:5993–5995, 1997.
Watt et al., *Blood*, 84:200–210, 1994.
Daniel et al., *Int. J. Cancer*, 55:303–310, 1993.
Teixeira et al., *Blood*, 84:211–219, 1994.
Barnett et al., *Molec. Cell. Biol.*, 13:1273–1282, 1993.
Thompsom et al., *J. Clin. Lab Anal.*, 5:344–366, 1991.
Öbrink, *Curr Opin Cell Biol.*, 9:616–626, 1997.
Rosenberg et al., *Cancer Res.*, 53:4938–4945, 1993.
Lin et al., *J. Biol. Chem.*, 264:14408–14414, 1989.
Öbrink, *BioEssays*, 13:227–234, 1991.
Williams et al., *Proc. Natl. Acad. Sci.*, 88:5533–5536, 1991.
Virji et al., *Mol. Microbiol.*, 5:941–950, 1996.
Kunath et al., *Oncogene*, 11:2375–2382, 1995.
Brümmer et al., *Oncogene*, 11:1649–1655, 1995.
Oikawa et al., *Biochem. Biophy. Res. Commun.*, 186:881–887, 1992.
Christ et al., *Immunol. Let.*, 58:159–165, 1997.
Hall et al., *Proc. Natl. Acad. Sci.*, 93:11780–11785, 1996.
Buckley et al., *J. Cell. Sci.*, 109:437, 1996.
Probert et al., *J. Immunol.*, 158:1941–1948, 1997.
Lundqvist et al., *Int. Immunol.* 7:1473–1480, 1996.
Coutelier et al., *Eur J. Immunol* 24:1383–1390, 1994.
Edlund and Obrink, *Fed of Euro Biochem Soc.* 327 (1):90–94, 1993.
Ciccone et al., *Immunol. Today*, 17:450–453, 1996.
Luengpailin et al., *Clinica Chimica Acta* 244:237–240, 1996.
Sopp and Howard, *Veterinary Immunology and Immunopathology* 56:11–25, 1997.
Watt et al., *Blood* 84(1):200–210, 1994.
Mollier et al., *Int J. Cancer* 65:740–745, 1996.
Morales, "Regulation of human intestinal intraepithelial lymphocyte cytolytic function by biliary glycoprotein (CD66a)" *Journal of Immunology*. 163:1363–1370. 1999.
Watt, et al., "Homophilic adhesion of human CEACAMI involves N–terminal domain interactions: structural analysis of the binding sit e." *Blood*. 98:1469–1473 (2001).

*Primary Examiner*—Christina Chan
*Assistant Examiner*—F. Pierre VanderVegt
(74) *Attorney, Agent, or Firm*—Wolf, Greenfield & Sacks,,P.C.

(57) ABSTRACT

The invention relates to compositions which bind T cell inhibitory receptor molecules and modulate T cell activity, and methods of using such compositions. Such compositions include biliary glycoprotein binding agents. Methods for modulating killer T cell activities, including cytotoxicity and proliferation also are provided.

14 Claims, 9 Drawing Sheets

T CELL INHIBITORY RECEPTOR COMPOSITIONS AND USES THEREOF

RELATED APPLICATIONS

This application is a divisional of Ser. No. 09/293,504, filed Apr. 15, 1999, and now pending. This application claims priority under 35 U.S.C. § 119(e) from U.S. provisional patent application Ser. No. 60/081,895, filed Apr. 15, 1998, the entire disclosure of which is incorporated herein by reference.

GOVERNMENT SUPPORT

This work was funded in part by the National Institutes of Health under Grant Numbers DK44319 and DK51362. The government may retain certain rights in this invention.

FIELD OF THE INVENTION

The invention relates to compositions which bind T cell inhibitory receptor molecules and modulate T cell activity.

BACKGROUND OF THE INVENTION

The biologic role of human intestinal intraepithelial lymphocytes (iIEL) and their functional relationship with the intestinal epithelial cell (IEC) remains incompletely characterized. Human iIELs have been variably shown to exhibit cytolytic function and possibly immunoregulatory function through the secretion of a variety of cytokines (Ebert, *Clin. Exp. Immunol.*, 82:81–85, 1990; Lundqvist et al., *J. Immunol.*, 157:1926–1934, 1996; Balk et al., *Science*, 253:1411–1415, 1991). Whether these functional activities are related to processes that may be unique to the gut associated lymphoid tissue such as oral tolerance and local immunosurveillance against IEC injury and neoplastic transformation is, however, unclear. Moreover, the molecules on the cell surface of iIELs and their IEC counterreceptors which regulate the functional activation of iIELs and which may be utilized in this special microenvironment are only beginning to be elucidated.

A significant fraction of human iIELs of both the small and large intestine are CD8-$\alpha\beta^+$ and CD45RO$^+$ T cells which express a limited array of $\alpha\beta$ and, to a lesser extent, $\gamma\delta$-T cell receptors (TCR) (Balk et al, 1991; Jarry et al., *Eur. J. Immunol.*, 20:1097–1103, 1990; Blumberg et al., *J. Immunol.*, 150:5144–5153, 1993; Van Kerckhove et al., *J. Exp. Med.*, 175:57–63, 1992; Chowers et al., *J. Exp. Med.*, 180:183–190, 1994). These phenotypic properties indicate that iIELs are memory cells which localize to the basolateral surface of IECs for the recognition of a limited number of antigens in the context of major histocompatibility complex (MHC) class I or class I-like molecules on the IEC. However, the majority of iIELs in mouse and human are CD28$^-$0 suggesting that other costimulatory molecules for TCR/CD3 complex-mediated activation may be important in providing necessary secondary signals for iIEL activation (Gelfanov et al., *J. Immunol*, 155:76–82, 1995; Gramzinski et al., *Int. Immunol.* 5:145–153, 1993; Russell et al., *J. Immunol.*, 157:3366–3374, 1996). Candidate costimulatory molecules for human iIELs include CD2 (Ebert, *Gastroenterology*, 97:1372–1381, 1989), CD101 (Russell et al., 1996), BY-55 (Anumanthan et al., *J.Immunol.*, 161:2780–2790, 1998) and $\alpha^E\beta_7$ (Parker et al., *Proc. Natl. Acad. Sci.*, 89:1924–1928, 1992) which are expressed by the majority of iIELs.

It has also become increasingly evident that in addition to activating costimulatory molecules, T cells can express a variety of molecules that deliver an inhibitory signal such that either the initial activation of the T cell is prevented or the activated state is downregulated. The former include the killer inhibitory receptors (KIR) which are expressed on a subset of T cells and bind specific types of major histocompatibility complex (MHC) class I molecules on the target cells (Lanier et al., *Immunology*, 7:75–82, 1995). The latter includes CTLA-4 (CD152) which, when expressed after T cell activation, binds either CD80 (B7.1) or CD86 (B7.2) on antigen presenting cells (Walunas et al., *J. Exp. Med.*, 183:2541–2550, 1996; Krummel et al., *J. Exp. Med.* 183:2533–2540, 1996). These inhibitory receptors characteristically contain immunoglobulin-like domains extracellularly and one or more immune receptor tyrosine-based inhibitory motifs (ITIM) in their cytoplasmic tails which consists of the consensus sequence I/L/VxYxxL/V (Vély et al., *J. Immunol.*, 159:2075–2077, 1997). In the case of CTLA-4, the ITIM is slightly modified to GxYxxM (Cambier, *Proc. Natl. Acad. Sci.*, 94:5993–5995, 1997). ITIM-containing receptors function in the recruitment of either the Src homology domain-containing protein tyrosine phosphatases, SHP-1 and SHP-2, or the SH2 domain-containing inositol polyphosphate 5-phosphatase, SHIP (Isakov, *Immunol. Res.*, 16:85–100, 1997). These phosphatases function in the dephosphorylation of signaling molecules recruited by immune receptor tyrosine-based activation motif (ITAM) bearing receptors like those contained in the CD3-$\gamma$, $\delta$, $\epsilon$ and $\zeta$ chains that associate with the TCR. As such, ITIM bearing receptors on T cells are predicted to downregulate activation events elicited by ITAM bearing receptors if both are ligated in close proximity to one another. Importantly, neither CTLA-4 nor CD80/CD86 have been observed on human iIELs or IECs of the small intestine, respectively.

SUMMARY OF THE INVENTION

It has now been discovered that biliary glycoprotein (BGP; also known as CD66a and C-CAM), a member of the carcinoembryonic antigen family (CEA), is an inhibitory receptor for activated T cells contained within the human intestinal epithelium. These studies suggest that, in a regional microenvironment that is predominantly CD28/CTLA4–CD80/CD86 negative, other receptor-ligand interactions may provide necessary downregulatory signals to limit T cell activation and immunopathology.

According to one aspect of the invention, methods for enhancing specifically the cytotoxicity or proliferation of killer T cells in a subject are provided. The methods include administering to a subject in need of such treatment an agent that selectively reduces cross-linking of biliary glycoprotein polypeptides in an amount effective to enhance the cytotoxicity or proliferation of killer T cells in the subject. In certain embodiments the agent is an antibody or antibody fragment which binds only a single biliary glycoprotein polypeptide. Preferred antibody fragments include Fab fragments. In other embodiments the agent comprises a ligand for the biliary glycoprotein polypeptide, wherein the ligand binds only a single biliary glycoprotein polypeptide. In preferred embodiments the ligand is fused to an immunoglobulin molecule or a fragment thereof, or is a soluble biliary glycoprotein molecule or fragment thereof. According to another aspect of the invention, methods for suppressing specifically the cytotoxicity or proliferation of killer T cells in a subject are provided. The methods include administering to a subject in need of such treatment an agent that selectively increases cross-linking of biliary glycoprotein polypeptides in an amount effective to suppress the activity of killer T cells in the subject. In certain embodiments the agent is an antibody, preferably a monoclonal antibody. In other embodiments the agent comprises a ligand for the biliary glycoprotein polypeptide which binds two or more biliary glycoprotein polypeptides. In preferred embodiments, the ligand is fused to an immunoglobulin molecule or a fragment thereof, or the ligand includes a biliary glycoprotein polypeptide or fragment thereof.

According to another aspect of the invention, a composition is provided. The composition includes an agent that selectively reduces cross-linking of biliary glycoprotein polypeptides in an amount effective to enhance cytotoxicity or proliferation of killer T cells in a subject, and a pharmaceutically-acceptable carrier. In certain embodiments the agent is an antibody or antibody fragment which binds only a single biliary glycoprotein molecule. Preferred antibody fragments include Fab fragments. In preferred embodiments, the agent comprises a ligand for the biliary glycoprotein polypeptide which binds only a single biliary glycoprotein polypeptide. Preferably such a ligand is fused to an immunoglobulin molecule or a fragment thereof. In certain embodiments ligand is biliary glycoprotein or a fragment thereof. Preferably the compositions are pharmaceutical compositions.

According to still another aspect of the invention, a composition is provided which includes an agent that selectively increases cross-linking of biliary glycoprotein polypeptides in an amount effective to suppress cytotoxicity or proliferation of killer T cells in a subject. The composition also include a pharmaceutically-acceptable carrier. In some embodiments the agent is an antibody, preferably a monoclonal antibody. In other embodiments the agent includes a ligand for the biliary glycoprotein polypeptide which binds two or more biliary glycoprotein polypeptides. Preferably the ligand is fused to an immunoglobulin molecule or a fragment thereof. In other preferred embodiments the ligand is biliary glycoprotein or a fragment thereof. Preferably the compositions are pharmaceutical compositions.

According to still other aspects of the invention, methods for enhancing specifically the cytotoxicity or proliferation of killer T cells also are provided. The methods include contacting a population of killer T cells with an agent that selectively reduces cross-linking of biliary glycoprotein polypeptides in an amount effective to enhance the cytotoxicity or proliferation of the killer T cells. The biliary glycoprotein binding agents are as described above in methods for enhancing killer T cell activity in a subject.

In another aspect of the invention, methods for suppressing specifically cytotoxicity or proliferation of killer T cells are provided. The methods include contacting a population of killer T cells with an agent that selectively increases cross-linking of biliary glycoprotein polypeptides in an amount effective to suppress the cytotoxicity or proliferation of the killer T cells. The biliary glycoprotein binding agents are as described above in methods for suppressing killer T cell activity in a subject.

According to another aspect of the invention, an isolated fusion protein is provided. The isolated fusion protein includes a biliary glycoprotein polypeptide or a fragment thereof fused to an immunoglobulin molecule or a fragment thereof. The components of the fusion protein can be fused directly, or a linker molecule such as a peptide can be interposed between the biliary glycoprotein component and the immunoglobulin component. Other polypeptides can be substituted for the immunoglobulin component as will be apparent to one of ordinary skill in the art. In certain embodiments, biliary glycoprotein (or fragment thereof) component of the fusion protein selectively binds a monoclonal antibody selected from the group consisting of 34B1, 5F4 and 26H7. Preferably the fragment of biliary glycoprotein is selected from the group consisting of the N-domain of CD66a, NA1B1 domains of CD66a, the NA1B1A2 domains of CD66a. The fragment of the immunoglobulin molecule preferably is the Fc portion of the immunoglobulin molecule.

According to another aspect of the invention, an isolated fusion protein is provided which includes two or more biliary glycoprotein polypeptides, or fragments thereof which bind biliary glycoprotein. The fusion protein is useful for selecting biliary glycoprotein binding agents which bind two (or more) biliary glycoprotein molecules, particularly those agents which cross-link biliary glycoprotein molecules.

According to yet another aspect of the invention, methods for identifying compounds which enhance or suppress killer T cell activity are provided. The methods include contacting a population of killer T cells which express biliary glycoprotein with a compound that binds biliary glycoprotein, and determining the cytotoxicity or proliferation of the population of killer T cells relative to a control. Compounds which increase the cytotoxicity or proliferation are compounds which enhance the killer T cell activity, and compounds which decrease the cytotoxicity or proliferation are compounds which suppress the killer T cell activity. In certain embodiments, the methods includes the steps of providing a biliary glycoprotein polypeptide or a fragment thereof, contacting the biliary glycoprotein polypeptide or a fragment thereof with a compound, and determining the binding of the compound to the biliary glycoprotein polypeptide or a fragment thereof. The compound is used in the foregoing methods for testing the increase or decrease of killer T cell cytotoxicity or proliferation.

In another aspect of the invention, methods for selectively treating a subject having a condition characterized by aberrant killer T cell activity are provided. The methods include administering to a subject in need of such treatment a pharmacological agent which is selective for biliary glycoprotein, in an amount effective to normalize the aberrant killer T cell activity.

In the foregoing aspects and embodiments of the invention, preferred killer T cells include $CD4^+$ T cells, $CD8^+$ T cells, NK cells, intestinal intraepithelial lymphocytes and peripheral blood T cells. Particularly preferred killer T cells are $CD8^+$ T cells.

The use of the foregoing compositions in the preparation of medicament also is provided. In preferred embodiments, the medicament is useful in the treatment of conditions related to immune system function, including autoimmune disease, cancer and transplantation.

These and other objects of the invention will be described in further detail in connection with the detailed description of the invention.

DETAILED DESCRIPTION OF THE INVENTION

Figure 1A:
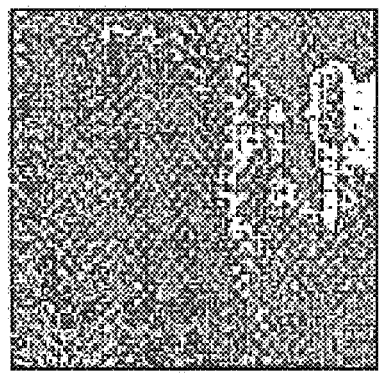
FIG. 1 depicts identification of three mAbs (34B1, 5F4 and 26H7) which recognize IECs but not resting iIELs.

Evidence for a role of human biliary glycoprotein (BGP, CD66a) as an inhibitory molecule on activated iIELs has been provided through the characterization of three monoclonal antibodies raised against an activated iIEL cell line. These data are especially relevant to iIELs as they suggest that other molecules such as biliary glycoprotein may contribute to downregulation of T cell activation in the absence of CTLA-4. These studies are also relevant to extending the function of biliary glycoprotein to an important role in immunoregulation of T lymphocytes in general given the observation that biliary glycoprotein is also expressed by activated human peripheral blood T cells.

Human biliary glycoprotein is a member of the CEA family of glycoproteins, part of the immunoglobulin supergene family, and encoded in a large cluster on chromosome 19 (Watt et al., *Blood*, 84:200–210, 1994; Daniel et al., *Int. J. Cancer*, 55:303–310, 1993; Teixeira et al., *Blood*, 84:211–219, 1994; Teixeira,1996; Barnett et al.,*Molec. Cell. Biol.*, 13:1273–1282, 1993). The CEA-cluster is highly related to the genetically linked, pregnancy specific gene cluster (Thompson et al., *J. Clin. Lab Anal.*, 5:344–366, 1991; Öbrink, *Curr Opin Cell Biol.*, 9:616–626, 1997). The CEA-subgroup of this family is serologically defined as CD66a (BGP or C-CAM), CD66b (CGM6), CD66c (NCA), CD66d (CGM1) and CD66e (CEA). These structurally related glycoproteins consist of a highly homologous membrane distal amino terminal IgV-like N-domain and variable numbers of membrane distal IgC2-like domains in the case of BGP, NCA, CGM6 and CEA. In contrast to human CEA, CGM6 and NCA, which are linked to the membrane by a glycosyl phosphatidyl-inositol anchor, CGM1 and BGP are type 1 transmembrane glycoproteins. Both of the latter exist as isoforms containing short or long cytoplasmic tails.

Biliary glycoprotein, and its mouse and rat homologues C-CAM (Rosenberg et al., *Cancer Res.*, 53:4938–4945, 1993; Lin et al., *J. Biol. Chem.*, 264:14408–14414, 1989; Öbrink, *BioEssays*, 13:227–234, 1991), have been regarded mainly as molecules which function in cell—cell adhesion that are expressed primarily by epithelial cells of the gastrointestinal tract and biliary tree, neutrophils and, more recently, B cells. Biliary glycoprotein also serves as a receptor for mouse hepatitis virus (Williams et al., *Proc. Natl. Acad. Sci.*, 88:5533–5536, 1991) and for Opa proteins of *Neisseria* species of bacteria (Virji et al.,*Mol. Microbiol.*, 5:941–950, 1996). It is of interest that ligation of biliary glycoprotein on epithelial cells may deliver a negative growth signal which may be decreased during tumor formation due to diminished expression of biliary glycoprotein (Rosenberg et al., 1993; Kunath et al., *Oncogene*, 11:2375–2382, 1995; Brummer et al., *Oncogene*, 11:1649–1655, 1995). Biliary glycoprotein also exhibits a high degree of alternate transcriptional processing resulting in at least eight potential alternate transmembrane transcripts. Two of these transcripts, BGPa and BGPb, encode a long cytoplasmic tail of 67 amino acids containing two ITIM motifs which suggest a role as inhibitory receptors (Öbrink, 1997). Indeed, this cytoplasmic tail, when tyrosine phosphorylated, is capable of binding SHP-1 in a mouse colon carcinoma cell line (Beauchemin et al., *Oncogene*, 783–790, 1996). Such interactions may account for the inhibitory growth effect of this molecule on epithelial cells.

The studies contained herein describe the unexpected finding that, whereas biliary glycoprotein is constitutively expressed by IECs, it is an activation molecule on T cells adjacent to the epithelium. The study of peripheral blood T cells, on the other hand, show the unexpected result that biliary glycoprotein is constitutively expressed at low levels and upregulated by T-cell activation. This difference between iIELs and PBTs suggests that biliary glycoprotein expression may be actively suppressed in the epithelium under normal conditions. The association of biliary glycoprotein with the activation state also resembles CTLA-4 expression.

Using cytotoxicity, which is a major function of iIELs, as a measure, it appears that biliary glycoprotein on activated iIELs functions as an inhibitory molecule for CD3-directed cytotoxic activity. In this manner, biliary glycoprotein should be considered as a killer inhibitory receptor. Although the ligand for biliary glycoprotein on the IEC is unknown, a candidate ligand is biliary glycoprotein itself or another CD66 family member in view of the known homophilic and heterophilic interactions between the CD66 group members (Watt et al., 1994; Oikawa et al., *Biochem. Biophy. Res.*, 186:881–887, 1992; Teixeira et al., 1994; Öbrink, 1997). It therefore can be hypothesized that ligation of biliary glycoprotein on the IEC by an activated iIEL can serve to function in the inhibition of IEC growth. Corollarily, the binding of biliary glycoprotein on the activated iIEL by BGP on the IEC can limit the activation of the T cell. In tumors of the epithelium where biliary glycoprotein expression has been observed to be diminished, the growth inhibition effect of the iIEL on the IEC might be lost (Brummer, 1995).

Thus the invention involves the finding that molecules which bind to biliary glycoprotein (i.e., "biliary glycoprotein binding agents") on killer T cells, such as antibodies, can inhibit or enhance the activity of killer T cells, such as cytotoxicity and/or proliferation. As used herein, "killer T cells" includes CD4$^+$ T cells, CD8$^+$ T cells, and NK cells. Biliary glycoprotein binding agents which increase cross-linking of biliary glycoprotein polypeptides increase the inhibitory signal of biliary glycoprotein, thereby suppressing the activity of killer T cells. Biliary glycoprotein binding agents which decrease cross-linking of biliary glycoprotein polypeptides decrease the inhibitory signal of biliary glycoprotein, thereby enhancing the activity of killer T cells. The invention also embraces molecules which enhance or suppress killer T cell activity but which do not function according to the cross-linking properties described above. For example, a particular biliary glycoprotein binding agent which suppresses the activity of killer T cells may bind biliary glycoprotein and increase the inhibitory signal of biliary glycoprotein without increasing cross-linking (e.g., by inducing a conformational change in biliary glycoprotein).

Modulation of killer T cell activity by molecules which bind biliary glycoprotein expressed on the surface of killer T cells is useful for specifically enhancing or suppressing an immune response in vivo, which may be useful for the treatment of conditions related to immune function including autoimmune disease, cancer, and transplantation (e.g., bone marrow or organs). Modulation of killer T cell activity also is useful in in vitro and/or non-therapeutic applications including determining whether T cells of a subject are functional (e.g. proliferation and/or cytotoxic functions), to determine if a treatment has rendered killer T cells non-functional, in experimental models of cancer, autoimmune disease, and transplantation, e.g., to determine the effects of increases or decreases in killer T cell function on particular organs or physiological processes, and to test for agents which increase or decrease killer T cell activity. Other uses will be apparent to one of ordinary skill in the art.

The molecules which bind biliary glycoprotein and modulate killer T cell activity (biliary glycoprotein binding agents) include antibodies and fragments thereof, ligands for biliary glycoprotein, fragments thereof and fusion proteins containing ligands or other biliary glycoprotein binding molecules. Still other biliary glycoprotein binding agents can be identified by screening compounds for the ability to enhance or suppress killer T cell activity, using assays described herein and those assays of T cell activity which are standard in the art. Exemplary methods for preparing fusion proteins useful according to the invention for modulating killer T cell activity are described herein; additional exemplary methods for preparing such fusion proteins are described in U.S. Pat. No. 5,434,131. The molecules which bind biliary glycoprotein can be used alone as a primary therapy or in combination with other therapeutics as a combination therapy to enhance the therapeutic benefits of other medical treatments.

The invention also involves agents which bind to biliary glycoprotein and/or fragments of the biliary glycoprotein and induce or suppress killer T cell activity. In addition to the uses described herein, such binding agents can be used in screening assays to detect the presence or absence of a biliary glycoprotein polypeptide, the presence or location of iIELs and in purification protocols to isolate iIELs and other killer T cells which express biliary glycoprotein. Likewise, such binding agents can be used to selectively target drugs, toxins or other molecules to killer T cells which express biliary glycoprotein. In this manner, killer T cells which express biliary glycoprotein can be treated with cytotoxic compounds, thereby reducing unwanted immune responses.

The biliary glycoprotein binding agents useful according to the invention, including antibodies and other polypeptides, are isolated agents. As used herein, with respect to biliary glycoprotein binding agents, the term "isolated" means that the agents are substantially pure and are essentially free of other substances with which they may be found in nature or in vivo systems to an extent practical and appropriate for their intended use. In particular, the agents are sufficiently pure and are sufficiently free from other biological constituents of their hosts cells so as to be useful in, for example, producing pharmaceutical preparations. Because an isolated biliary glycoprotein binding agent may be admixed with a pharmaceutically acceptable carrier in a pharmaceutical preparation, the biliary glycoprotein binding agents may comprise only a small percentage by weight of the preparation. A biliary glycoprotein binding agent is nonetheless substantially pure in that it has been substantially separated from the substances with which it may be associated in living systems.

According to one embodiment, the biliary glycoprotein binding agent used in the invention is an intact anti-biliary glycoprotein monoclonal antibody in an isolated form, preferably in a soluble form, or in a pharmaceutical preparation. An intact monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided unto subregions referred to as variable regions and constant regions. As used herein the term "monoclonal antibody" refers to a homogenous population of immunoglobulins which specifically bind to an epitope (i.e. antigenic determinant) of human biliary glycoprotein.

The invention, therefore, includes the use of antibodies or fragments of antibodies having the ability to selectively bind to biliary glycoprotein, particularly as expressed on the cell surface of killer T cells, such as intestinal intraepithelial lymphocytes and activated peripheral blood lymphocytes. Antibodies include polyclonal and monoclonal antibodies, prepared according to conventional methodology. Examples include the monoclonal antibodies 34B1, 5F4 and 26H7 described in the Examples. Additional antibodies which are reactive with biliary glycoprotein, particularly those raised against biliary glycoprotein expressed on killer T cells, can be prepared according to standard methods.

Antibodies can be prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies may be used, for example, to identify tissues expressing protein or to purify protein. Antibodies also may be coupled to specific labeling agents for imaging or to cytotoxic agents, including, but not limited to, methotrexate, radioiodinated compounds, toxins such as ricin, other cytostatic or cytolytic drugs, and so forth.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to biliary glycoprotein. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention, using methods such as those described in Hart et al., *J. Biol. Chem.* 269:12468 (1994). Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to biliary glycoprotein or a fragment thereof. This process can be repeated through several cycles of reselection of phage that bind to biliary glycoprotein or a fragment thereof. Repeated rounds lead to enrichment of phage bearing particular sequences. DNA sequence analysis can be conducted to identify the sequences of the expressed polypeptides. The minimal linear portion of the sequence that binds to biliary glycoprotein or a fragment thereof can be determined. One can repeat the procedure using a biased library containing inserts containing part or all of the minimal linear portion plus one or more additional degenerate residues upstream or downstream thereof. Thus, biliary glycoprotein can be used to screen peptide libraries, including phage display libraries, to identify and select peptide biliary glycoprotein binding agents for modulating killer T cell activity. Preferably, the biliary glycoprotein binding agents are characterized as to their ability to cross-link biliary glycoprotein. Such binding molecules can also be used, as described, for screening assays, for diagnostic assays, for purification protocols or for targeting drugs, toxins and/or labeling agents (e.g. radioisotopes, fluorescent molecules, etc.) to cells, especially killer T cells, which express biliary glycoprotein on the cell surface. Drug molecules that would disable or destroy cells which express such biliary glycoprotein or a fragment thereof are known to those skilled in the art and are commercially available. For example, the immunotoxin art provides examples of toxins which are effective when delivered to a cell by an antibody or fragment thereof. Examples of toxins include ribosome-damaging toxins derived from plants or bacterial such as ricin, abrin, saporin, *Pseudomonas* endotoxin, diphtheria toxin, A chain toxins, blocked ricin, etc.

Additionally small polypeptides including those containing the biliary glycoprotein binding fragment (CDR3 region) may easily be synthesized or produced by recombinant means to produce a biliary glycoprotein binding agent useful according to the invention. Such methods are well known to those of ordinary skill in the art. Peptides can be synthesized for example, using automated peptide synthesizers which are commercially available. The peptides can be produced by recombinant techniques by incorporating the DNA expressing the peptide into an expression vector and transforming cells with the expression vector to produce the peptide.

The sequence of the CDR regions, for use in synthesizing peptide biliary glycoprotein binding agents, may be determined by methods known in the art. The heavy chain variable region is a peptide which generally ranges from 100 to 150 amino acids in length. The light chain variable region is a peptide which generally ranges from 80 to 130 amino acids in length. The CDR sequences within the heavy and light chain variable regions which include only approximately 3–25 amino acid sequences may easily be sequenced by one of ordinary skill in the art. The peptides may even be synthesized by commercial sources.

To determine whether a peptide binds to biliary glycoprotein any known binding assay may be employed. For example, the peptide may be immobilized on a surface and then contacted with labeled biliary glycoprotein. The amount of biliary glycoprotein which interacts with the peptide or the amount which does not bind to the peptide may then be quantitated to determine whether the peptide binds to biliary glycoprotein. A surface having the aforementioned anti-biliary glycoprotein monoclonal antibodies immobilized thereto may serve as a positive control.

Screening of biliary glycoprotein binding agents also can be carried out utilizing a competition assay. If the biliary glycoprotein binding agent being tested competes with an anti-biliary glycoprotein monoclonal antibody, as shown by a decrease in binding of the monoclonal antibody, then it is likely that the agent and the anti-biliary glycoprotein monoclonal antibody bind to the same, or a closely related, epitope. Still another way to determine whether an agent has the specificity of the anti-biliary glycoprotein monoclonal antibodies described above is to pre-incubate the monoclonal antibody with biliary glycoprotein with which it is normally reactive (i.e., binds), and then add the agent being tested to determine if the agent being tested is inhibited in its ability to bind biliary glycoprotein. If the agent being tested is inhibited then, in all likelihood, it has the same or a functionally equivalent epitope and specificity as the anti-biliary glycoprotein monoclonal antibodies.

Using routine procedures known to those of ordinary skill in the art, one can determine whether a biliary glycoprotein binding agent is useful according to the invention by determining whether the agent is one which modulates killer T cell proliferation or cytotoxicity in an in vitro assay such as measuring release of TNF from killer T cells or by $^{51}$Cr release assay (see, e.g., Herin et al., *Int. J. Cancer* 39:390–396, 1987). Other assays are described in the Examples and elsewhere herein.

The polypeptides (e.g. antibodies) and other biliary glycoprotein binding agents described above can also be used immunotherapeutically for killer T cell sensitive disorders in humans. The term "immunotherapeutically" or "immunotherapy" as used herein in conjunction with the biliary glycoprotein binding agents denotes both prophylactic as well as therapeutic administration. Thus, the peptides can be administered to high-risk subjects in order to lessen the likelihood and/or severity of a killer T cell sensitive disease, such as a tumor, transplant rejection or autoimmune disease, or administered to subjects already evidencing such diseases.

In certain aspects the invention encompasses methods for modulating specifically the cytotoxicity or proliferation of killer T cells in situ. The method includes administering to a subject in need of such treatment an agent which binds selectively a biliary glycoprotein polypeptide in an amount effective to enhance or suppress the cytotoxicity or proliferation of the killer T cells in the subject. As shown in the Examples, the activity of killer T cells is subject to specific modulation because killer T cells express biliary glycoprotein. Methods for modulating specifically the cytotoxicity or proliferation of killer T cells also are provided wherein a population of killer T cells is contacted with a biliary glycoprotein binding agent. When a biliary glycoprotein binding agent is administered to a subject or contacted to a population of killer T cells, the inhibitory activity of biliary glycoprotein is modulated. Biliary glycoprotein binding agents which increase or decrease killer T cell activity can be selected using the assays described herein and according to standard killer T cell cytotoxicity and proliferation assays, such as mixed lymphocyte reactions, chromium release assays, TNF release assays, and thymidine incorporation assays. It is believed that a monovalent biliary glycoprotein binding agent will inhibit the inhibitory signal of biliary glycoprotein by reducing cross-linking of biliary glycoprotein polypeptides expressed by killer T cells, and that a multivalent biliary glycoprotein binding agent (having two or more biliary glycoprotein binding sites) will increase the inhibitory signal of biliary glycoprotein in killer T cells by increasing cross-linking of biliary glycoprotein polypeptides expressed by killer T cells.

By definition, the term "in situ" encompasses and includes the terms in vivo, ex vivo and in vitro. The compositions of the invention are useful for many in vitro purposes. For example, the compositions of the invention are useful for screening compounds which inhibit killer T cell proliferation or cytotoxicity. Such a screening assay may be performed in vitro by setting up cell proliferation or cytotoxicity assays including a biliary glycoprotein binding agent which increases killer T cell proliferation or cytotoxicity and a population of killer T cells. Potential killer T cell proliferation or cytotoxicity inhibitors may be added to the mixture and the effect on proliferation or cytotoxicity may be measured. Agents which increase proliferation or cytotoxicity of killer T cell can be screened using similar assays.

Thus methods for identifying compounds which bind biliary glycoprotein (or modulate activation of biliary glycoprotein by other molecules such as natural ligands) and enhance or suppress killer T cell activity are provided according to the invention. Other in vitro uses, such as research purposes, are known to those of ordinary skill in the art.

Ex vivo uses also will be readily identified by those of skill in the art. Ex vivo uses include, for example, the stimulation of proliferation or cytotoxicity of killer T cells which have been removed from a mammalian subject and which are subsequently returned to the body of the mammalian subject.

The present invention also includes methods for treating a condition characterized by aberrant killer T cell activity, such as cytotoxicity or proliferation. The methods involve the step of administering to a subject having such a condition a pharmacological agent which selectively binds biliary glycoprotein and modulates a killer T cell activity, in an amount effective to increase or decrease T-cell proliferation or cytotoxicity.

A "condition characterized by aberrant killer T cell activity" as used herein is any condition associated with adverse physiological consequences in which an increase or decrease of killer T cell function, embodied by an increase or decrease in killer T cell proliferation or cytotoxicity, results in an improvement of the adverse physiological consequences. Such conditions include disorders of the immune system, such as immunodeficiency, autoimmunity and transplant rejection, as well as disorders involving undesirable cellular invasion by microorganisms or undesirable cell growth such as tumors.

The biliary glycoprotein binding agents are administered in effective amounts. As used herein, an "effective amount" of a biliary glycoprotein binding agent is an amount which is sufficient to modulate (increase or decrease) biliary glycoprotein inhibitory function, resulting in a modulation of killer T cell proliferation or cytotoxicity. Modulating biliary glycoprotein inhibition of killer T cell activity is sufficient to produce the desired effect in which the symptoms associated with the conditions characterized by aberrant killer T cell activity are ameliorated or decreased. Preferably an effective amount of the peptide is a therapeutically effective amount for modulating killer T cell proliferation or cytotoxicity in vivo. Generally, a therapeutically effective amount may vary with the subject's age, condition, weight and gender, as well as the extent of the disease in the subject and can be determined by one of skill in the art as a matter of routine experimentation. The dosage may be adjusted by the individual physician in the event of any complication. A therapeutically effective amount typically will vary from about 0.01 mg/kg to about 500 mg/kg, were typically from about 0.1 mg/kg to about 200 mg/kg, and often from about 0.2 mg/kg to about 20 mg/kg, in one or more dose administrations daily, for one or several days (depending of course of the mode of administration and the factors discussed above).

One of skill in the art can determine what an effective amount of a biliary glycoprotein binding agent is by determining the ability of the agent to modulate killer T cell proliferation or cytotoxicity in an in vitro assay. Exemplary assays for measuring the ability of a biliary glycoprotein binding agent to modulate killer T cell proliferation or cytotoxicity are provided in the Examples and have been discussed above. The exemplary assays are predictive of the ability of a biliary glycoprotein binding agent to modulate killer T cell activity in vivo and/or ex vivo and, hence, can be used to select agents for therapeutic applications.

According to the invention, a biliary glycoprotein binding agent may be administered in a pharmaceutically acceptable composition. In general, pharmaceutically-acceptable carriers for antibodies, antibody fragments, and other biliary glycoprotein binding agents (including small molecules such as those derived from combinatorial libraries) are well-known to those of ordinary skill in the art. As used herein, a pharmaceutically-acceptable carrier means a nontoxic material that does not interfere with the effectiveness of the biological activity of the active ingredients, i.e., the ability of the agent to modulate killer T cell activity. Pharmaceutically acceptable carriers include diluents, fillers, salts, buffers, stabilizers, solubilizers and other materials which are well-known in the art. Exemplary pharmaceutically acceptable carriers for peptides are described in U.S. Pat. No. 5,211,657. The agents of the invention may be formulated into preparations in solid, semi-solid, liquid or gaseous forms such as tablets, capsules, powders, granules, ointments, solutions, depositories, inhalants and injections, for oral, parenteral or surgical administration. The invention also embraces pharmaceutical compositions which are formulated for local administration, such as by implants.

According to the methods of the invention the agents can be administered by injection, by gradual infusion over time or by any other medically acceptable mode. The administration may, for example, be intravenous, intraperitoneal, intramuscular, intracavity, subcutaneous or transdermal. Preparations for parenteral administration includes sterile aqueous or nonaqueous solutions, suspensions and emulsions. Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

The methods of the invention also encompass administering biliary glycoprotein binding agents in conjunction with conventional therapies for treating immune system disorders. For example, the methods of the invention may be practiced simultaneously with conventional treatments. The particular conventional treatment depends, of course, on the nature of the disorder. When, for example, the condition related to aberrant killer T cell activity is a tumor, a conventional mode of treatment is chemotherapy. The agents of the invention which increase killer T cell activity (e.g., decrease biliary glycoprotein inhibitory activity) may be administered in conjunction with chemotherapy in the treatment of the tumor in order to provide enhanced tumoricidal effects. Other immune system diseases can be treated concurrently with the biliary glycoprotein binding agents described herein and other molecules which bind T cells and affect T cell function, such as CTLA4Ig fusion proteins, as described in U.S. Pat. No. 5,434,131.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Materials and Methods

Antibodies: The 34B1, 26H7 and 5F4 monoclonal antibodies (mAbs) were produced by immunizing BALB/c mice with the activated human mucosal lymphocyte line, 191E, as previously described (Russell et al., 1996). Three intraperitoneal injections and a final intravenous injection of $5 \times 10^6$ lymphocytes were given at two-week intervals. Three days after the intravenous immunization, splenocytes were isolated and fused with NS1 murine myeloma cells in the presence of PEG (m.w. 1450) as described previously. Hybridomas were selected with aminopterin-containing medium, and hybridoma supernatants were screened by indirect immunoperoxidase staining of frozen intestinal and tonsillar tissue sections. Positive hybridomas were subcloned twice by limiting dilution, and ascites containing the antibody was produced by intraperitoneal injection of the hybridoma cells into pristane-treated BALB/c mice. The isotypes of 34B1 (IgG1), 26H7 (IgG1) and 5F4 (IgG1) were determined by ELISA using murine isotype-specific mAb (Boehringer Mannheim, Indianapolis, Ind.). W6/32 is a mouse IgG2a mAb specific for human MHC class I (kindly provided by Dr. Jack Strominger, Dana-Farber Cancer Institute, Boston, Mass.). OKT3 (IgG2a is a mouse anti-human CD3 mAb (kindly provided by Dr. Robert Finberg, Dana-Farber Cancer Institute, Boston, Mass.). TS2/18 (kindly provided by Dr. Llyod Klickstein, Brigham and Women's Hospital) is an anti-CD2 mAb (mouse IgG2a). OKT11 (kindly provided by Dr. Ellis Reionherz, Dana-Farber Cancer Institute) is an anti-CD2 mAb (mouse IgG29). OKT4 and OKT8 are mouse IgG2a mAbs specific for human CD4 and CD8-α, respectively (obtained from American Type Culture Collection, Bethesda, Md.). UCHT1, directly conjugated to phycoerythrin, is a mouse IgG1 mAb specific for human CD3-ε (Dako, Denmark). The MA22 (CD66a; clone YG-C94G7; IgG1), MA26 (CD66a; clone 4.3.17; IgG1), MA27 (CD66e; clone 26/5/1; IgG2a), MA28 (CD66e; clone 26/3/13; IgG1), MA30 (CD66c; clone 9A6; IgG1), MA41 (CD66b; clone BIRMA17c; IgG1), MA61 (CD66b; clone 80H3; IgG1), MA76 (CD66ae; clone 12-140-4; IgG1), MA79 (CD66b; clone B13.9; MA81 (CD66b; clone G10F5; IgG1), MA83 (CD66e; clone b7.8.5; IgG1), MA84 (CD66clone COL-1; IgG2a, MA86 (CD66acde; clone B6.2; IgG1) and MA91 (CD66e; clone T84.66; IgG1) are mouse mAbs which were obtained from the VIth Leukocyte Typing Workshop, Osaka, Japan. The isotype matched mouse IgG1 negative control mAb was purchased from Kakopatts (Copenhagen, Denmark) or Cappel (West Chester, Pa.). mAbs were purified by affinity purification and protein-A or G sepharose columns by standard methods.

Cells and Cell Lines: Peripheral blood mononuclear cells (PBMC) were obtained by Ficoll-Hypaque gradient centrifugation using standard methods. Peripheral blood T cells were stimulated by cultivating PBMCs for 72 hours at 37° C. in RPMI-1640 (Gibco, Grand Island, N.Y.) containing penicillin/streptomycin (100 units/ml), 10 mM Hepes pH 7.4, 10% fetal calf serum and 1 μg/ml phytohemagglutin-P (PHA-P) (Murex Diagnostics, Dartford, England). Human iIEL cell lines EEI-10 (small intestine), EEI-5 (small intestine) and CLI (large intestine) were generated as previously described (Christ et al., Immunol. Let., 58:159–165, 1997) and maintained by stimulation with 1 μg/ml PHA-P cells in RPMI-1640 containing 10% human serum (type AB, Sigma, St. Louis, Mo.), 5 units/ml rIL-4 (Genzyme, Cambridge, Mass.) and 2 nM rIL-2 (a kind gift from Ajinomoto Co., Ltd., Japan) and irradiated PBMC as feeder cells. HT29 is a human intestinal epithelial cell (IEC) line obtained from the ATCC. COS is a monkey kidney fibroblast cell line. These latter cell lines were maintained in RPMI-1640 containing 10% heat-inactivated fetal calf serum (Gibco), penicillin and streptomycin, nonessential amino acids and 10 mM HEPES (complete medium) at 37° C. in 5% $CO_2$.

Transfectants: The BGPx' molecule was constructed as follows. The N terminal domain and the transmembrane/ cytoplasmic domains of human BGPc were each amplified separately by PCR with the primer pairs BGPAMP-S: caucaucaucauaagcttatggggcacctc (SEQ ID NO:1) and NTM-AS: gccattttcttggggcabctccgggtatac (SEQ ID NO:2); NTM-S: gtataccggagctgccccaagaaaatggc (SEQ ID NO:3) and BGPTRANS-CYT-AS: cuacuacuacuaagactatgaagttggttg (SEQ ID NO:4), respectively, where the NTM primers were hybrids of the 3' end of the N terminal domain and the 5' end of the transmembrane domain. The PCR reaction consisted of 5 µl 10× Taq buffer (10 mM Tris-HCl pH 8.3, 50 mM KCl, 0.1% gelatin), 3 µl 1.5 mM $MgCl_2$, 1 µl 200 µM of each dNTP, 1 µM of each primer, 1 Unit Taq polymerase and 1 µg cDNA in a final volume of 50 µl. The PCR reaction was carried out at conditions of 94° C. for 10 min, followed by 25 cycles of 94° C. for 1 min, 55° C. for 1 min, and 72° C. for 2 min, plus a final extension time of 10 min at 72° C. After passing the PCR products through S-300 columns, 5 µl of each PCR product were used in a second PCR. After the PCR products had annealed, the BGPAMP and TRANS-CYT AS primers were added to the reaction mix and the PCR reaction carried out as described above. The resulting PCR product was cloned into the pAMP 1 vector using the CloneAMP system as detailed by the manufacturer (Gibco-BRL, Gaithersburg, Md.), transformed into DH5α competent bacteria and positive transformants selected by PCR. The resulting BGPx' cDNA was extracted and sequenced by standard methods. The BGPx' cDNA was digested with EcoRI and NotI restriction enzymes and subcloned into the pcDNA1/Amp vector (Invitrogen, Carlsbad, Calif.). The BGPx' cDNA in this vector and the pSV2neo plasmid (Clontech, Palo Alto, Calif.) were linearized with XhoI and BamHI, respectively, and electroporated into CHO cells at a ratio of 15:1, selected in G418 and on the FACS cell sorter to create a stable CHO-BGPx' cell line as described earlier (Watt et al., 1994). CHO cells stably transfected with BGPx', Neomycin (Neo), BGPc (Watt et al., 1994)) and BGPa (Oikawa et al., Biochem. Biophys. Res. Commun., 186:881–887, 1992) and HeLa cells stably transfected with CEA, CGM1, NCA and CGM6 have been previously described (Daniel et al., 1993).

Flow Cytometry: For one color immunofluorescence, approximately 1×10⁶ cells were stained with 1 µg of the primary mAb for 30 minutes on ice. Cells were then washed with phosphate buffered saline (PBS) containing 2% fetal calf serum or 0.2% bovine serum albumin and 0.02% sodium azide (WB) followed by incubation for 30 minutes with 1 µg of a goat-anti-mouse fluorescein isothiocyanate labeled secondary antibody (Zymed, San Francisco, Calif.) diluted in WB. The cells were washed with WB and either examined fresh or resuspended in 1% paraformaldehyde in PBS. The stained and fixed cells were analyzed on either an Epics V flow cytometer (Coulter, Hialeah, Fla.) or a FAC-SCalibur (Becton-Dickinson, Sunnyvale, Calif.). For two color immunofluorescence, staining was performed as described above except that after incubation with primary conjugate, the stained cells were blocked for 20 minutes in PBS containing 20% normal mouse serum followed by incubation with a directly conjugated mAb.

Immunohistochemistry: Tissue samples were mounted in OCT compound (Ames Co., Elkart, Ind.), frozen in liquid nitrogen or in a cryostat and stored at −70° C. Frozen tissue sections 4 µm thick were fixed in acetone for 5 minutes, air dried, and stained by an indirect immunoperoxidase method (Canchis et al., Immunology, 80:561–569, 1994) using avidin-biotin-peroxidase complex (Vector Laboratories, Burlingame, Calif.) and 3-amino-9-ethylcarbazole (Aldrich Chemical Co., Inc., Milwaukee, Wis.) as the chromogen.

COS Cell Expression Cloning: A cDNA library was constructed in the pCDM8 vector using poly(A)⁺ RNA from resting and activated human PBT and from NK cells in the vector pAEXF (Hall et al., Proc. Natl. Acad. Sci., 93:11780–11785, 1996). For the first round of selection, COS cells were transfected via the DEAE-Dextran procedure (Seed et al., Proc. Natl. Acad. Sci., 84:3365–3369, 1987) with 0.2 µg of library DNA per 100 mm dish. After 40 hr, cells were harvested, incubated with 34B1 mAb (1:500 dilution of ascites), washed, and panned on anti-IgG1 coated plates as previously described (Seed et al., 1987; Freeman et al., J. Immunol., 143:2714–2722, 1989). Episomal DNA was prepared from adherent cells, re-introduced into E. coli, transfected into COS cells by polyethylene glycol-mediated fusion of spheroplasts (Seed et al., 1987), and the panning with 34B1 mAb repeated. Individual plasmid DNAs were transfected into COS cells via the DEAE-Dextran procedure and analyzed after 72 hr for cell surface expression by indirect immunofluorescence and flow cytometry.

Radiolabeling, Immunoprecipitation and Electrophoresis: COS cells, 96 hours after transient transfection, were removed nonnenzymatically from plastic Petri dishes and labeled with Na—[$^{125}$I] by the lactoperoxidase catalyzed method as previously described (Balk et al., Science, 265:259–262, 1994). After washing, radiolabeled cells were lysed in immunoprecipitation buffer (IPB) containing 150 mM sodium chloride, 50 mM Tris pH 7.8, 10 mM Iodoacetamide, 1 mM EDTA (1 mM PMSF and 1 µg/ml each of leupeptin, pepstatin, aprotinin, and chymostatin with 1% Nonidet P40 as a detergent). Cells were lysed on ice for 30–60 minutes followed by centrifugation at 14,000 g for 15 minutes at 4° C. The supernatant from the centrifugation was then centrifuged at 100,000 g at 4° C. in a TL-100 ultracentrifuge. The supernatant from this centrifugation was incubated with 20 µl of packed protein-A Sepharose beads and rocked overnight at 4° C. After preclearing with either an irrelevant isotype matched mAb or normal mouse serum coupled to either protein-A or protein-G Sepharose beads, specific immunoprecipitations were performed by rocking overnight at 4° C. with mAbs coupled to protein-A or G sepharose (Pharmacia, Piscataway, N.J.) and the beads washed with IPB containing detergent. For N-glycanase digestions, immunoprecipitates were suspended in 0.25 M Na—$HPO_4$ and 1 mM EDTA after boiling in 0.8% β-mercaptoethanol and 0.5% SDS. Immunprecipitates were then either treated with 1 unit of N-glycanase (Genzyme, Boston, Mass.) or mock treated at 37° C. overnight and resuspended in Laemmli buffer containing reducing agents. Solubilized immunoprecipitates were then resolved in 12.5% polyacrylamide gels in the presence of SDS.

Production of Soluble Recombinant Proteins: Details of the pIG plus vector (R&D Systems Europe Ltd., Abingdon, UK) containing the Fc genomic fragment of human IgG1 and incorporating the hinge (H), CH2 and CH3 domains of the construction of the CD66a-Fc soluble proteins containing the N, NA1B1 and NA1B1A2 extracellular domains, Muc-18-Fc and NCAM-Fc have been described previously (Teixeira et al., 1994; Buckley et al., *J. Cell. Sci.*, 109:437, 1996; Teixeira, 1996). NCAM-FC, Muc-18-Fc (R&D Systems) and the CD66-Fc (N-Fc, NA1B1-Fc and NA1B1A2-Fc) cDNAs were transfected into COS cells and the secreted soluble protein purified on protein-A Sepharose as previously described (Watt et al., 1994; Teixeira et al., 1994).

Analysis of Antibody Binding to Soluble Recombinant Proteins: As previously described (Teixeira et al., 1994), ninety-six well flat bottom microtiter plates (Immulon 3) were coated with 100 µl anti-human Fc (Sigma, St. Louis, Mo.) at a final concentration of 1 µg/ml in 10 mM Tris-HCl pH 8 overnight at 4° C. Wells were washed four times, blocked for 1 hr at room temperature with 0.25% BSA, 0.05% Tween 20 in PBS (pH 7.4), and coated overnight at 4° C. with 50 µl of soluble Fc construct at a final concentration of 10 µg/ml in PBS. After washing the wells four times with PBS, 50 µl of mAb at varying dilutions in PBS were added per well for 1–2 h at room temperature. Wells were washed with PBS four times and 50 µl of 1:4000 dilution of alkaline phosphatase conjugated goat anti-mouse Ig (Boehringer-Mannheim) in PBS were added per well for 1 h at room temperature. The wells were washed four times with PBS and 200 µl paranitrophenyl phosphate substrate were added (Sigma) and developed for 15–45 min at room temperature. The absorbance at 405 nm was determined. All experiments were carried out in triplicate and repeated at least twice.

Redirected Lysis: Cytotoxicity was evaluated as previously described (Probert et al., *J. Immunol.*, 158:1941–1948, 1997). Briefly, the P815 mouse mastocytoma cell line was labeled with 100 µCi [$^{51}$Cr] (New England Nuclear, Boston, Mass.) at 37° C. for 30 minutes. $2 \times 10^3$ radiolabeled cells, in 100 µl complete medium, were added to 100 µl of varying concentrations of effector T cells in 100 µl of complete medium in triplicate in a 96 well V-bottom plate. Prior to addition of target cells, the effector cells were incubated for 20 minutes at room temperature with the OKT3 mAb (200 ng/ml of purified antibody) and/or 34B1, 26H7 or 5F4 mAbs (either 1:600 dilution of ascites or varying concentrations of purified antibody). After 5 hours, 100 µl of supernatant were removed for analysis in a γ-counter (LKB Wallac Clini Gamma 1272, Finland). Spontaneous and maximal release were measured by incubating target cells with medium or 1% Nonidet-P40, respectively. Percent cytotoxicity was calculated using the formula (experimental release–spontaneous release)×100/(maximal release–spontaneous release).

Statistics: Differences between samples were evaluated with a non-paired, Student's T-test using the Sigma Stat (Jandel Scientific, San Rafael, Calif.) program.

Example 1

Constitutive Expression of the 34B1-Related Antigen on the Cell Surface of Normal Human IECs During the development of iIEL specific mAbs, which were obtained by immunizing mice with an iIEL T-cell line from human small intestine propagated in vitro, it was noted that a certain fraction of the mAbs stained IECs as shown by immunohistochemistry of normal human small intestine. Three of these mAbs and the characterization of the antigen that they recognized were of particular interest, as described below.

Figure 1B:
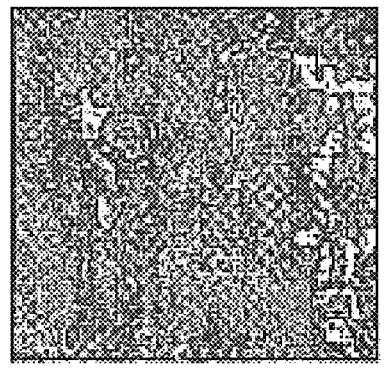
Figure 1C:
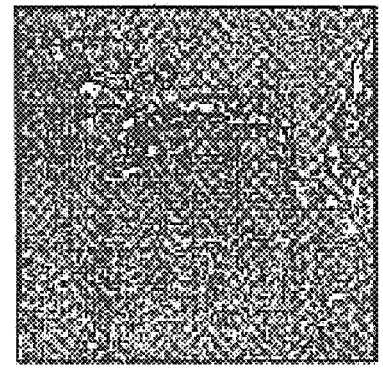

FIG. 1 depicts identification of three mAbs (34B1, 5F4 and 26H7) which recognize IECs but not resting iIELs. Panels A–C show immunohistology of normal human large intestine stained with the 34B1 (panel A), 5F4 (panel B) and 26H7 (panel C) mAbs with binding detected by subsequent incubation with a goat anti-mouse horseradish peroxidase conjugated antibody as described in the Materials and Methods. The precipitated brown reaction product indicates specific staining on the enterocyte. [Magnification: 20×]. Staining with normal mouse serum was negative (data not shown).

Staining of human intestinal tissue sections showed that these three mAbs (34B1, 26H7 and 5F4) only stained IECs (FIG. 1). This in vivo tissue staining with these antibodies appeared to be on the cell surface as confirmed by flow cytometry analysis of a normal human IEC line, HT29. Since these three antibodies did not stain iIELs in situ, as determined by immunohistochemistry (FIG. 1), or immediately after isolation as determined by flow cytometry (data not shown), it was suspected that iIELs, activated during the process of in vitro cultivation, expressed neoantigens that were constitutively expressed by IECs.

Example 2

Figure 2A:
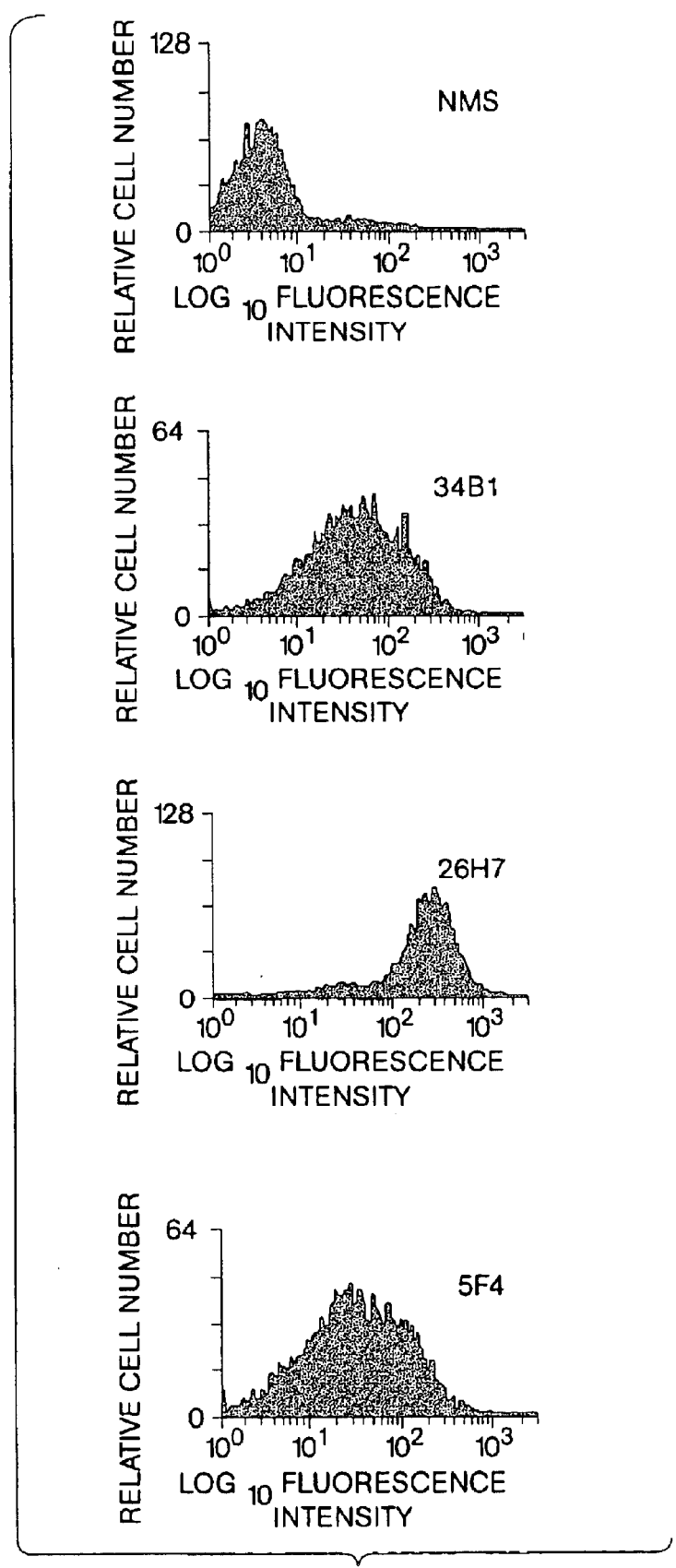
FIG. 2 shows that iIELs and PBTs express an antigen that is recognized by the 34B1, 5F4 and 26H7 mAbs after activation.

The 34B1-Related Antigen is an Activation Antigen on Normal Human iIELs and Peripheral Blood T Cells To determine whether iIEL cell lines expressed neoantigens that were shared with IECs, the staining of iIELs was examined after in vitro cultivation with PHA-P. One color flow cytometry analysis was performed of an activated iIEL cell line derived from the small intestine, EEI-5, as described in FIG. 1. As shown in FIG. 1A, iIELs in situ and freshly isolated iIELs (data not shown) did not stain with the 34B1, 26H7 and 5F4 mAbs. However, after maintenance in vitro as continuous cell lines with PHA-P activation every 10–14 days, all of the iIELs expressed the antigen recognized by these three mAbs (FIG. 2A). Staining of an iIEL T-cell line established from the small intestine, EEI-5, which was 90% CD8$^+$ and 10% CD4$^+$ as shown in FIG. 1B indicates that all iIEL expressed the antigen recognized by the three mAbs after in vitro activation. The three mAbs exhibited slightly different staining patterns suggesting that they either recognized a different molecule or a different epitope on the same molecule. Similar observations were made with an iIEL T cell line prepared from the large intestine, CLI, which was 40% CD8$^+$, 30% CD4$^+$ and 30% double negative (CD4$^-$CD8$^-$) consistent with the in vivo phenotype of iIELs in this tissue site (Lundqvist et al., *Int. Immunol.* 7:1473–1480, 1996; data not shown).

Figure 2B:
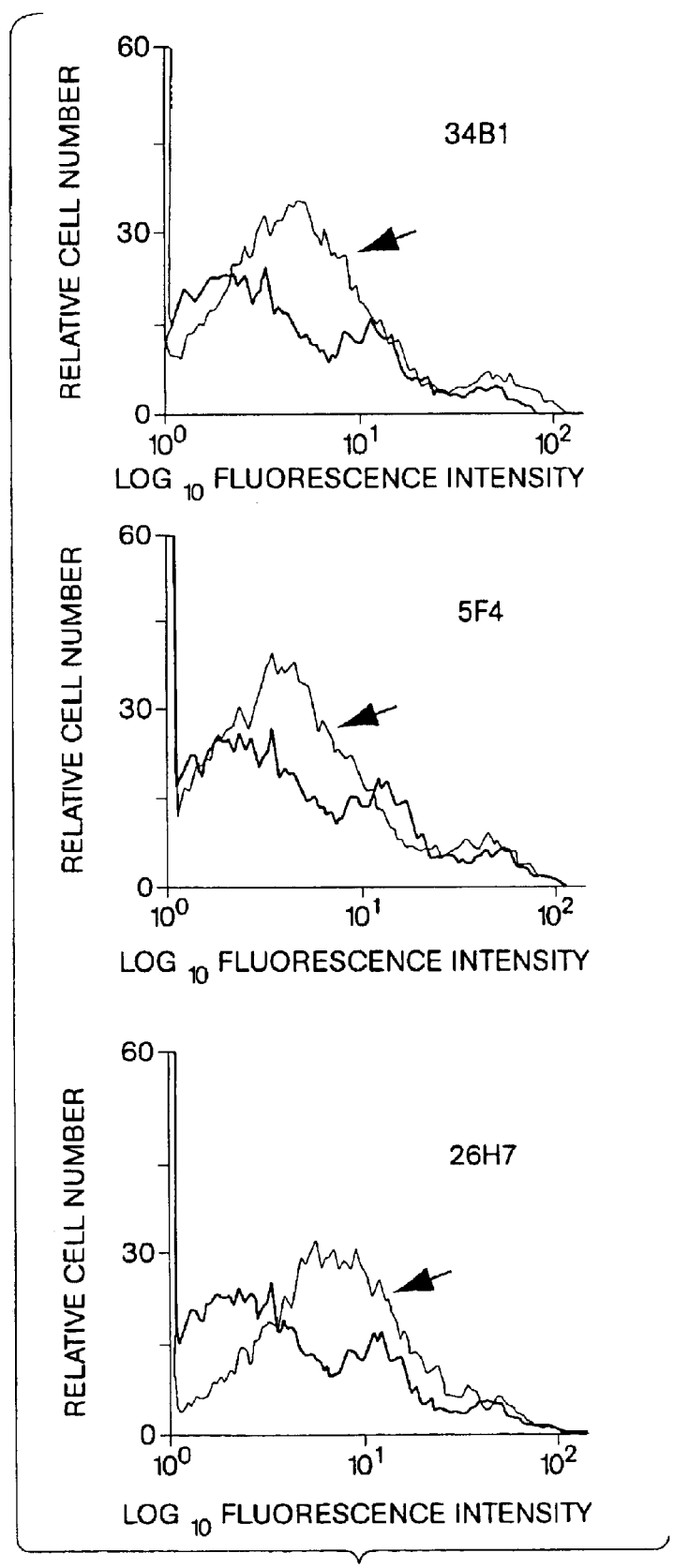

These characteristics were, however, not confined to iIELs since PBTs expressed the 34B1-related antigen and upregulated this expression after stimulation with PHA-P in vitro. FIG. 2B shows the two-color fluorescence analysis of normal PBTs, before and after three days of stimulation with 1 µg/ml PHA-P, with the 34B1, 5F4 and 26H7 mAbs after gating on the CD3-positive lymphocytes and after subtracting background staining with directly conjugated, isotype matched control antibody. The thick black line shows staining of PBTs without PHA-P stimulation and the thin black line (arrow) with PHA-P stimulation. Prior to PHA-P stimulation, a discrete population of T cells exhibited increased staining with the 34B1, 5F4 and 26H7 mAbs (FIG. 2B). After PHA-P stimulation, a small but significant shift in the intensity of staining of the entire population with all three mAbs was observed. Thus, the 34B1-related antigen is an activation antigen on both normal human T cells in the intestinal epithelium and peripheral blood.

Example 3

The 34B1-Related Antigen is Expressed on Epithelial Cells, B Cells and Granulocytes in a Wide Variety of Organs The data above suggested that the 34B1-related antigen was expressed by epithelial cells of the intestine and activated T cells. A limited organ survey of the distribution of this cellular expression was therefore examined. As can be seen in Table 1, the antigen(s) recognized by the 34B1, 26H7 and 5F4 mAbs were similarly expressed within a wide variety of tissues suggesting that the molecule(s) of interest had a functional role in diverse organ systems. All three mAbs consistently recognized an antigen on epithelial cells of the small and large intestine, biliary tree, kidney, skin and thymus. In addition, scattered granulocytes in several organs and cells within germinal centers of tonsils, which were consistent with B cells, also stained positive. The staining of granulocytes was confirmed by immunohistochemical analysis of peripheral blood granulocytes (data not shown). Thus, these results, together with the phenotypic studies described above, suggested that the 34B1-related antigen(s) was primarily expressed by a wide variety of epithelial cell types, B and T lymphocytes, granulocytes and natural killer (NK) cells, based upon staining of an NK cell line (data not shown).

TABLE I

Tissue Staining of the 34B1-Related mAbs

| Tissue | Staining Pattern |
|---|---|
| Kidney | Proximal tubules (+) |
|  | Glomeruli (+) |
|  | Endothelium (+) |
| Liver | Biliary canaliculi (+) |
|  | Bile ducts (+): luminal surfaces |
| Lymph Node | Sinusoids (+): Granulocytes/Platelets |
| Skin | Epidermis (−) |
|  | Eccrine/Sweat glands (+) |
| Small Intestine | Enterocyte (+): Villous > Crypt |
|  | Goblet cells (−) |
|  | Granulocytes (+) |
| Thymus | Hassal corpuscles (+) |
| Tonsil | Germinal centers (+) |
|  | Epithelium (+) |

Staining of all tissues is shown as described in the Materials and Methods. For each tissue, cellular staining was graded as either absent (−) or present (+) as defined by a pathologist.

Example 4

Identification of the 34B1-Related Antigen as Biliary Glycoprotein (BGP)

To identify the molecule recognized by the 34B1-related mAbs, the 34B1 mAb was used to clone the cDNA which coded for the cognate antigen of the 34B1 mAb by COS cell expression cloning after transfection with a mixture of three cDNA libraries from resting and activated human PBTs and NK cells. These cDNA libraries were utilized because previous studies showed expression of the antigen recognized by the 34B1, 26H7 and 5F4 mAbs in these cell types. Transiently transfected COS cells were subjected to three rounds of immunoselection and panning with the 34B1 mAb. After the third round of panning, 17 of 50 randomly-selected E. coli transformants contained plasmids with a 3.3 kb-insert. The inserts in these plasmids were similar by restriction digest analysis. COS cells transfected with these plasmids were specifically stained with the 34B1 mAb. One of these plasmids, pPAN3.1, was selected for further characterization.

Figure 4:
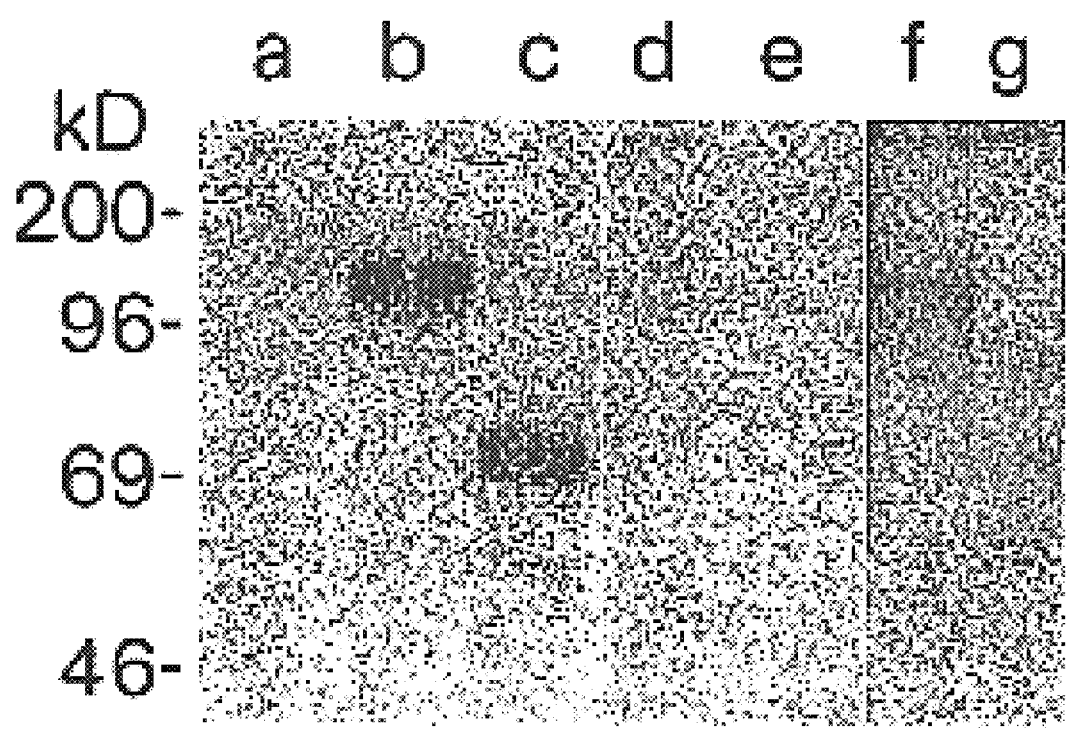
FIG. 4 shows that the 34B1-related mAbs specifically immunoprecipitate BGP on COS cell transfectants and activated iIELs.

This plasmid directed the translation, when transfected into COS cells, of a 120-kD glycoprotein which was specifically recognized by the 34B1 and 5F4 mAbs and that resolved as a major band of approximately 70-kD and several minor bands of lower molecular weight after digestion with N-glycanase (FIG. 4). Cell surface proteins of COS cells transiently transfected with the pPAN3.1 vector encoding BGPb (lanes a–c) or the pCDM8 vector (lanes d and e) and the activated iIEL cell line, EEI-10 (lanes f and g) were radiolabeled with [$^{125}$I] and immunoprecipitated with either the 34B1 mAb (lanes b, c, d, e, f and g) or normal mouse serum (lane a) and the immunoprecipitates resolved under reducing conditions with (lanes c, e and g) or without (lanes a, b, d and f) prior N-glycanase treatment. Identical observations were made with the 5F4 and 26H7 mAbs (data not shown). A similar glycoprotein was immunoprecipitated from radiolabeled cells surface iIEL proteins by all three mAbs (FIG. 4). Complete DNA sequencing of this cDNA on both strands revealed a sequence that was 97% identical to the 'b' splice variant of BGP or CD66a (Gen Bank accession #X14831) with all the differences occurring outside the coding region. Since the cDNA predicted a polypeptide backbone of 58 kD, the data in FIG. 4 suggest that several of the carbohydrate modifications were relatively resistant to N-glycanase digestion.

BGPs are members of the immunoglobulin supergene family that consists of an N-terminal immunoglobulin V-(IgV) related domain, that is highly homologous to the N-domains of other carcinoembryonic antigen (CEA) or CD66 family members, followed by several IgC2-related domains A1 and B1, and the A2, Y or Z domains which are unique to BGP isoforms (Watt et al., 1994; Oikawa et al., 1992; Teixeira, 1994; Barnett et al., 1993; Thompson, 1991).

Figure 3A:
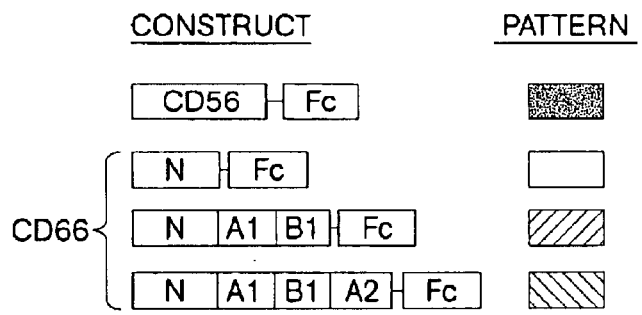
FIG. 3 shows that the N-domain of BGP is the cognate antigen of the 34B1-related mAbs.
Figure 3B:
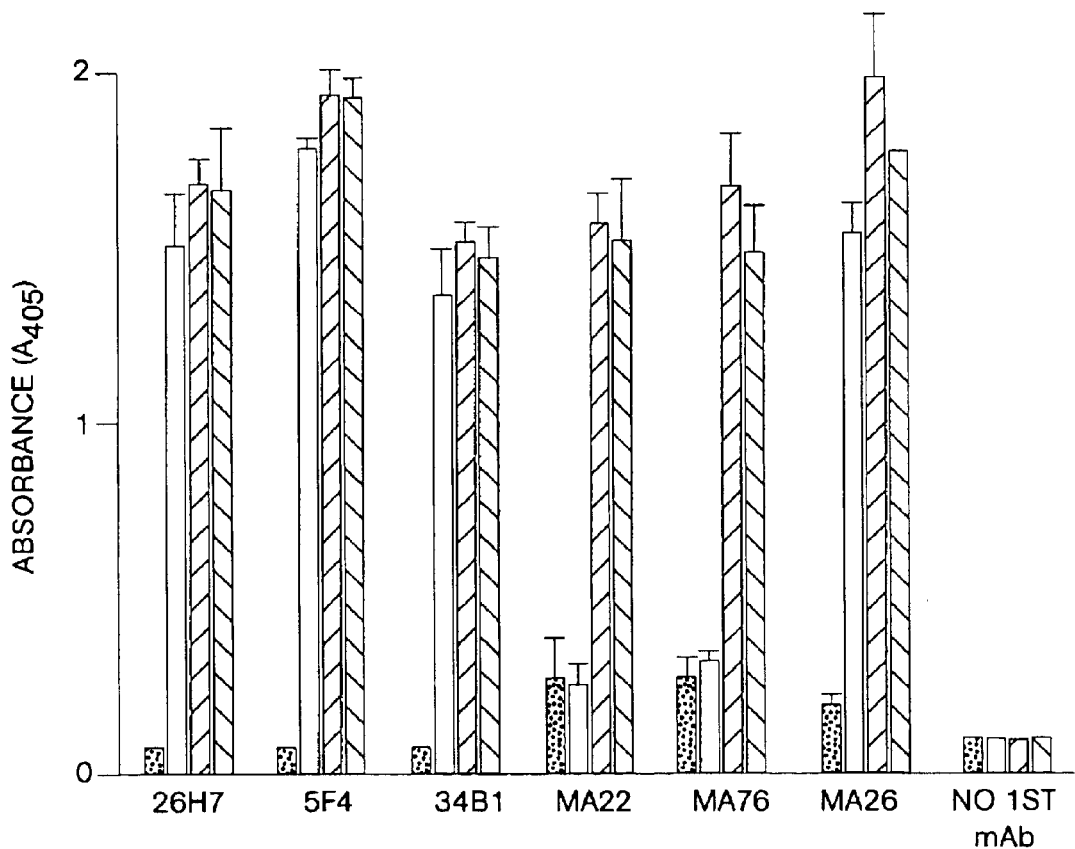

In order to confirm that the 34B1-related mAbs were reactive with BGP and to define the specific protein domain to which these mAbs were directed, the antibodies were tested in a binding assay with Fc-fusion proteins containing either the N-domain of CD66a, NA1B1 domains of CD66a, the NA1B1A2 domains of CD66a, and N-CAM (CD56) as a negative control. FIG. 3A is a schematic diagram of the Fc-fusion proteins used in the ELISA to test the mAbs as described in the Materials and Methods. Fc-fusion proteins containing the N, NA1B1 and NA1B1A2 domains of CD66a or N-CAM (CD56) as a negative control were tested in an ELISA as described in the Materials and Methods with the 34B1, 5F4 and 26H7 mAbs in comparison to the positive control antibodies, MA22, MA76 and MA26 (FIG. 3B). As can be seen in FIG. 3, these studies confirmed the recognition of BGP (CD66a) by the three mAbs and showed that all three mAbs reacted with the N-domain.

Figure 5:
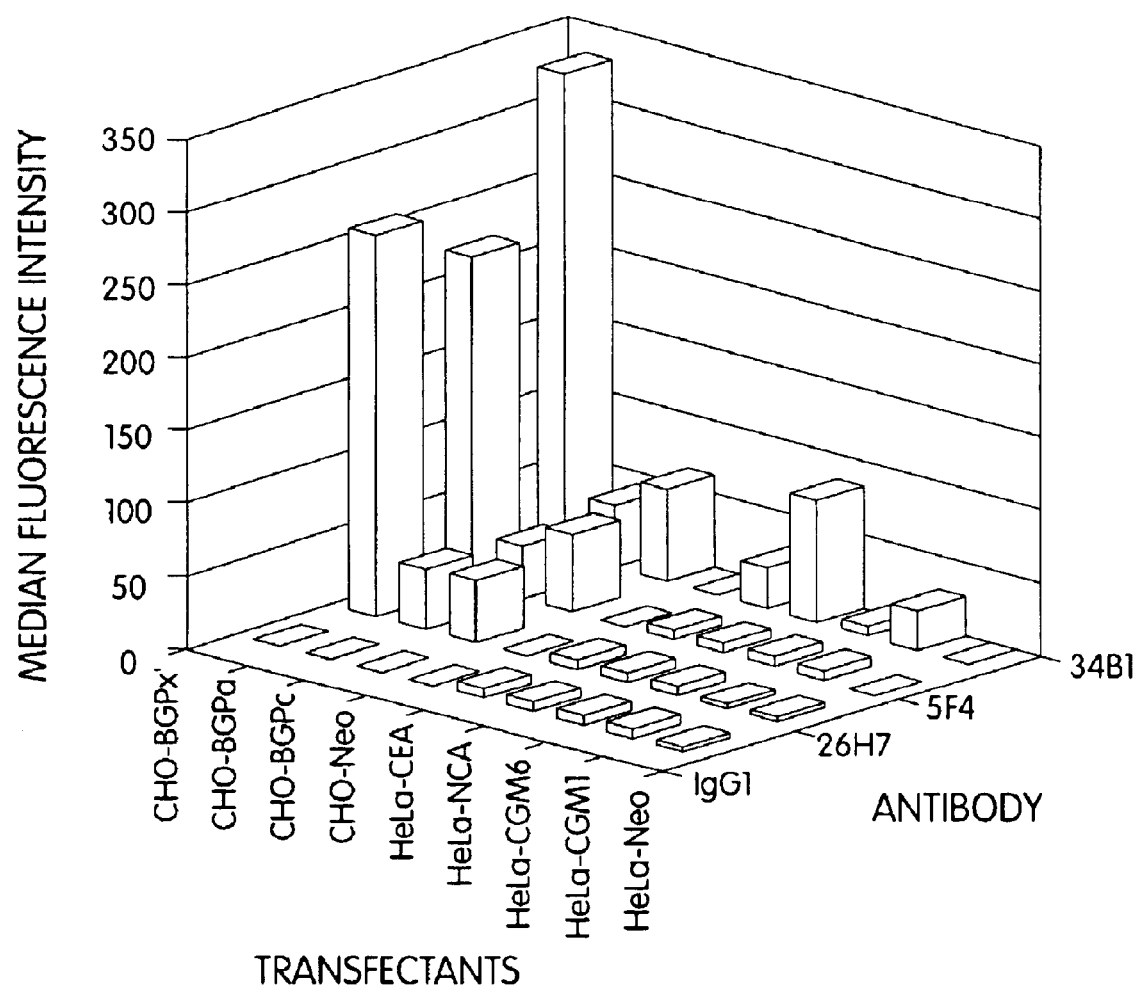
FIG. 5 depicts the specificity of the anti-BGP mAbs for other CD66 family members.

In order to further confirm that the cognate antigen of the 34B1-related mAbs was BGP, the three mAbs were tested for their ability to stain CHO cells stably transfected with several splice variants of BGP (BGPa, BGPc and BGPx') and HeLa cells transfected with other members of the CD66 serologic cluster including CD66b (CEA gene related member 1, CGM1), CD66c (CEA gene related member 6, CGM6), CD66d (Nonspecific cross reacting antigen, NCA) and CD66e (CEA). FIG. 5 shows the flow cytometric analysis of BGPa, BGPc and BGPx' transfectants of CHO, and CEA, NCA, CCGM6 and CGM1 transfectants of HeLa cells in comparison to the mock (Neo) transfectants after staining with either the 34B1, 5F4 and 26H7 mAbs or isotype matched IgG1 antibody as a negative control. All transfectants were positively stained with control mAbs specific for the transfected cDNA (data not shown). Except for CGM1 (CD66b), the 34B1 mAb stained all the CD66 family members tested including all of the CD66a splice variants. The 26H7 and 5F4 mAbs, however, only stained the CD66a splice variants suggesting they were likely specific for the N-domain of this molecule. These results, together with those from phenotyping and the distribution of BGP on epithelial cells, granulocytes, B cells, T cells and NK cells described above and previously reported (Thompson et al., 1991; Möller et al., 1996), clearly identify the N-domain of BGP as the cognate antigen of the 34B1, 26H7 and 5F4 mAbs and that, in addition, the 34B1 mAb recognizes other CD66 forms.

Example 5 iIELs Express only CD66a Isoform

Figure 6:
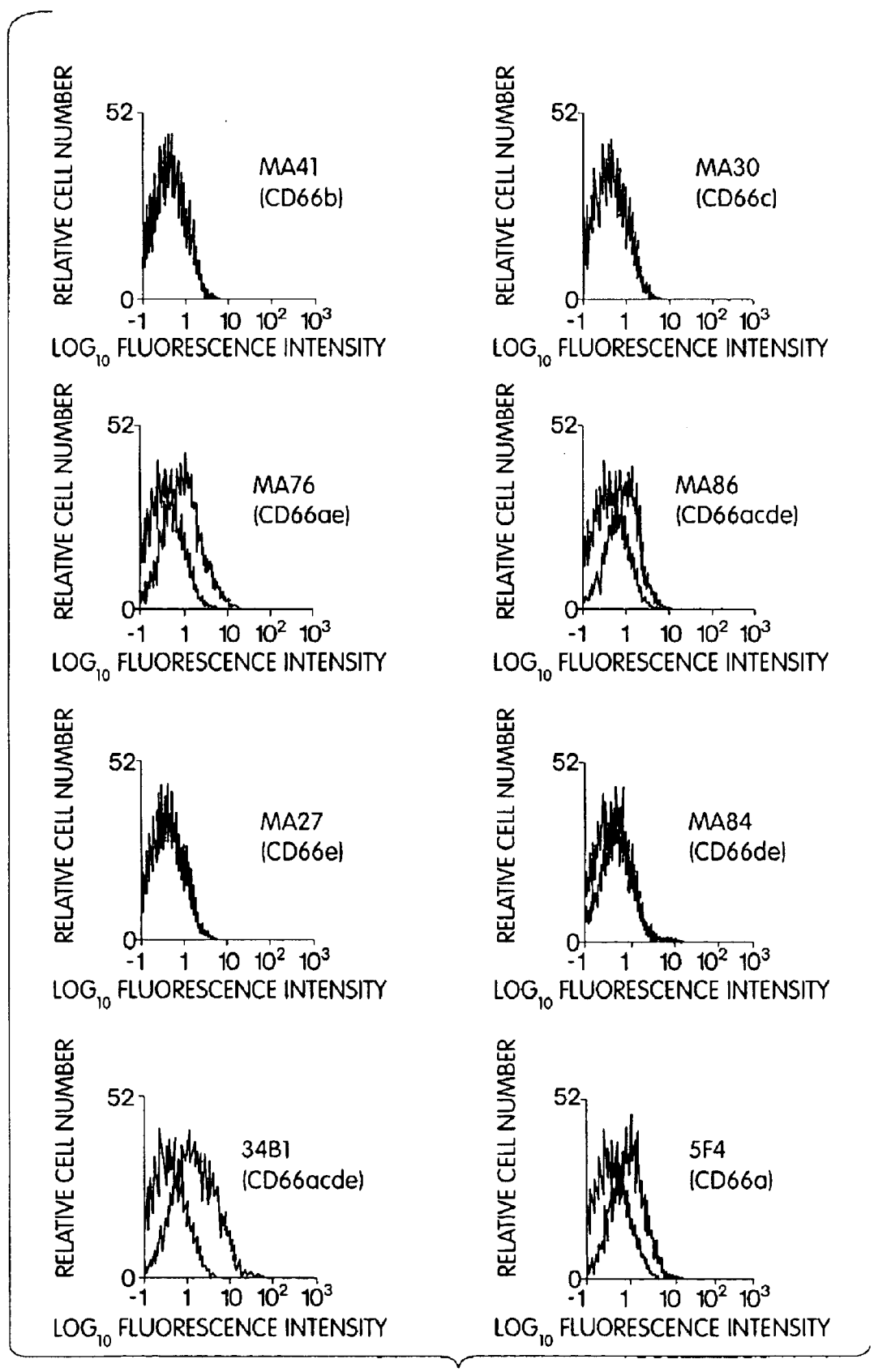
FIG. 6 shows an analysis of CD66 isoform expression by activated human iIELs.

Activated human iIELs were stained with a panel of mAbs that have been presented at the Sixth International Workshop on Monoclonal Antibodies and which are specific for all of the CD66 isoforms. The human iIEL cell line from small intestine, EEI-10, was stained 8 days after activation with a series of anti-CD66 mAbs as described in the Materials and Methods. Each panel shows an overlay of the CD66 specific mAbs with the staining obtained with normal mouse serum as a negative control. The specificity of the mAbs for the CD66 isoforms is indicated in the panels. Activated iIELs do not express any CD66 isoforms other than CD66a based upon staining with a large panel of mAbs specific for CD66a–e (mabs MA27, MA28, MA30, MA41, MA61, MA76, 79, MA81, MA83, MA84, MA86 and MA91 (FIG. 6).

To draw a further similarity between BGP and ITIM containing KIRs, the effects of the CD66a specific mAbs on the pattern of tyrosine phophsorylated proteins after ligation of CD3 was assessed with th4e Eei-10 cell line. iIELs ($1\times10^6$) were incubated in 100 $\mu$l RPMI-1640 containing 0.1% bovine serum albumin (Sigma) with 100 ng/ml OKT3 mAb and either 10 $\mu$g/ml of the 5F4 mAb or 10 $\mu$g/ml normal IgG1 in the presence of 20 $\mu$g/ml goat anti-mouse IgG antibody (Pierce, Rockford, Ill.) as crosslinker. After either 2 or 8 minutes incubation at 37° C., the reaction was stopped with 1 ml PBS containing 10 mM $Na_2VO_3$ (Sigma), the pellet incubated on ice for 30 minutes in 100 $\mu$l lysis buffer containing 0.2x PBS, 100 $\mu$M $Na_2VO_3$, 1 mM PMSF, 5 mM iodoacetamide and 20 $\mu$g/ml aprotinin and Laemmli buffer added with reducing agents. The lysates were boiled for 5 minutes, resolved by SDS-PAGE on a 10% gel, Western transferred to Immobilon filters, immunoblotted with the PY20 mAb (Zymed, San Francisco, Calif.) and developed with a horseradish peroxidase conjugated goat anti-mouse antibody (Zymed) and enhanced chemiluminescence. Cross-linking of CD3 with the OKT3 mAb in the presence of the 5F4 mAb, in comparison to an isotype controlled antibody, resulted in a significant alteration in the kinetics and level of phosphorylation suggesting that a phosphatase was activated as a consequence of BGP crosslinking.

Example 6

BGP Functions as a Killer Inhibitory Receptor for iIELs

The observation that BGP was expressed on activated iIELs as defined by staining with the BGP-specific mAbs, 34B1, 26H7 and 5F4 was unique and unexpected since BGP has previously been primarily viewed as a molecule expressed on epithelial cells and granulocytes and involved in cell—cell adhesion and regulation of epithelial cell growth. The function of BGP on iIELs and T cells in general was, however, unknown. Importantly, the cytoplasmic tail of the BGPa and BGPb splice variants, but not CD66b–e, contain two ITIM domains within the cytoplasmic tail separated by 21 amino acids raising the possibility that BGP might function as an inhibitory molecule on T cells (Beauchemin et al., 1996; Öbrink, 1997). In order to define the role of the BGP antigen in T cell function, the effects of the three mAbs on the function of iIELs was examined.

Figure 7:
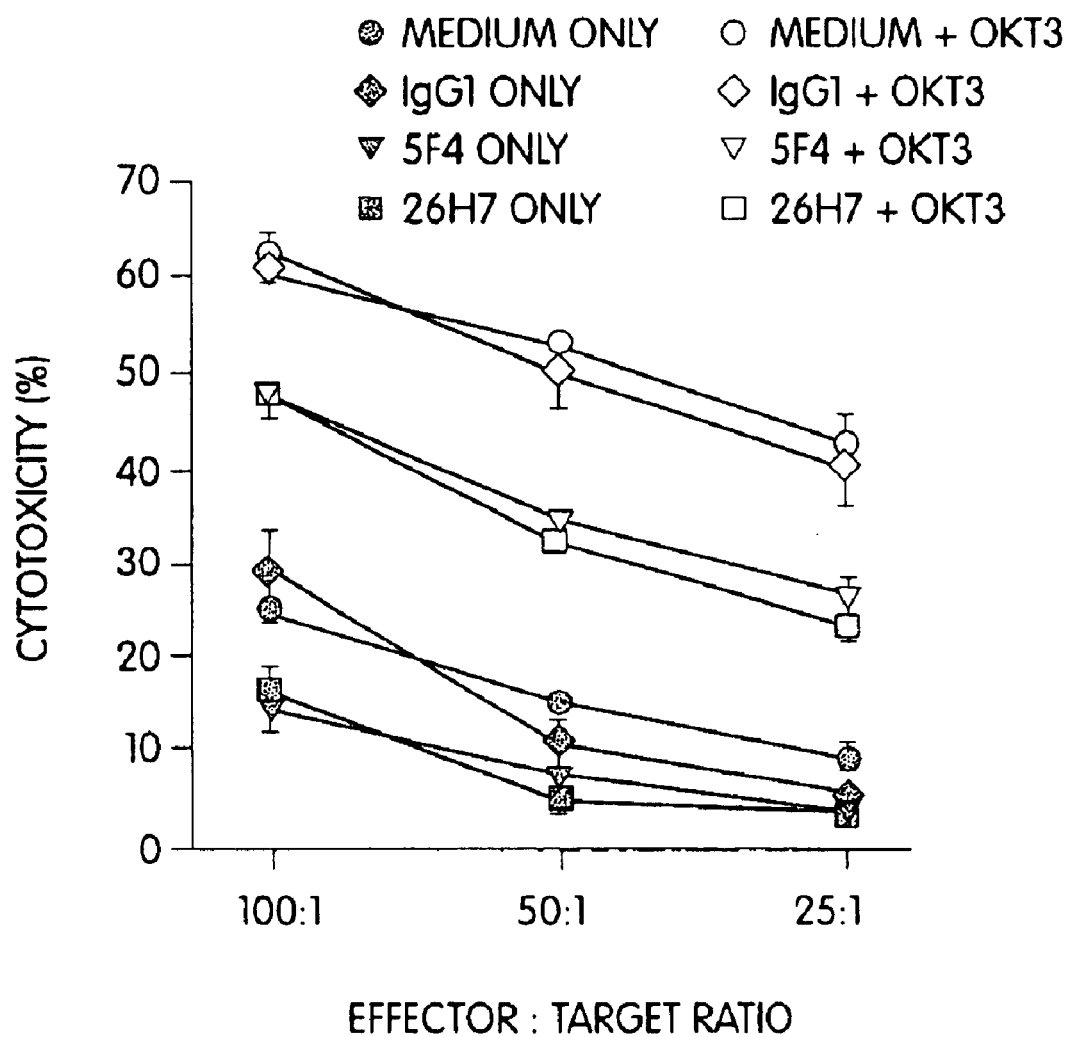
FIG. 7 depicts inhibition of anti-CD3 directed and lymphokine activated killer activity of iIELs by anti-BGP antibodies.

A major function of activated iIELs is as cytolytic effector cells. Therefore, the effects of the three mAbs on the cytolytic function of iIELs was examined in a redirected lysis assay, the results of which are depicted in FIG. 7. The anti-CD3 directed lysis (OKT3) of the KJ-3 iIEL cell line was examined as described in the Materials and Methods in the absence or presence of either the CD66a specific mAbs, 5F4 or 26H7, or an isotype matched IgG1 antibody at a concentration of 100.0 $\mu$g/ml at effector:target ratios of 100:1, 50:1 and 25:1. The cytolysis in the absence of added antibodies (medium) and presence of the test antibodies alone (26H7, 5F4 and control IgG1) are also shown. The standard error of the mean for each measurement is indicated. The data presented in FIG. 7 is representative of six experiments. When an iIEL cell line, EEI-10, derived from normal human small intestine, was examined in a redirected lysis assay with the P815 mouse mastocytoma cell line as a target cell, significant cytotoxicity was elicited with, but not without, anti-CD3 cross-linking using the OKT3 mAb (FIG. 7). Neither the 34B1, 26H7 nor 5F4 mAbs at a variety of different concentrations were able to stimulate cytolysis of the P815 cell line indicating that cross-linking BGP did not directly activate iIELs. However, cross-linking BGP with all three anti-BGP mAbs resulted in a significant inhibition of the anti-CD3 directed cytolysis of the P815 cell line in comparison to an isotype matched IgG1 control antibody which exhibited no inhibition. The 5F4 mAb inhibited the lysis by 22%, 35% and 38% at effector:target ratios of 100:1, 50:1 and 25:1, respectively. The inhibition by the control antibody at similar effector:target ratios was −4%, 5% and 5%. Moreover, the anti-CD3 directed cytolysis was not inhibited by a CD2-specific mAb, TS 2/18, which would be expected to inhibit CD58-like interactions with the P815 cell line, suggesting that the inhibition by the anti-CD66a mAbs was not likely due simply to an effect on adhesion. Thus, cross-linking of BGP inhibited the anti-CD3 directed cytolytic activity of iIELs.

When iIELs were harvested early after cytokine treatment, a significant amount of cytolysis was observed against the P815 cell line consistent with cytokine induced killer activity (lymphokine activated killer activity, LAK), a property previously described for iIEL. To test whether this cytolytic activity was also subject to inhibition by the anti-BGP mAbs, the iIEL cell line was exposed to the P815 cell line as target in the presence or absence of the BGP specific mAbs, a pool of the BGP specific mAbs or normal IgG1. The effects of the anti-BGP specific mAbs 34B1, 26H7 and 5F4 on cytolysis of the p815 cell line by the EEI-10 iIEL cell line was examined at an effector target ratio of 25:1. The cytolysis of the p815 cell line was not affected by the irrelevant IgG1 antibody at either 2 $\mu$g/ml or 6 $\mu$g/ml. The inhibition of the cytotoxicity was significant for all anti-BGP antibodies (5F4, p=0.15; 26H7, p=0.048, 34B1, p=0.004; pool, p=0.0016). The anti-BGP mAbs inhibited the cytolytic activity of the iIEL cell line by as much as 70% using the pool of mAbs at 2 $\mu$g/ml each, and up to 50% inhibition at doses of individual mAbs of 2 $\mu$g/ml, indicating the lymphokine activated killer activity of iIELs was also subject to inhibition by the anti-BGP antibodies.

Example 7

Anti-BGP Antibodies can Inhibit the BGP Inhibitory Signal in an Allogenic Mixed Lymphocyte Reaction Human peripheral blood mononuclear cells (donor A) were irradiated (5000 Rads) and cococultivated with an equivalent number of nonirradiated peripheral blood mononuclear cells prepared by Ficoll-Hypaque gradient centrifugation at a total concentration of $2 \times 10^5$ cells per well of a 96-well U-bottom plate in a total volume of 200 $\mu$l in quadruplicate. After 96 hours, 0.5 $\mu$Ci of [$^3$H]-thymidine was added per well for 18 hours of incubation and the plates harvested and counted. The culture conditions contained no additives (medium) or various concentration of diluted ascites (mouse anti-human BGP monoclonal antibodies 34B1 and 5F4) or normal mouse serum. The experimental data depicted in Table II are representative of 5 experiments. The mean±SE is presented. The augmentation of T cell proliferation in the presence of anti-BGP antibodies is consistent with the inhibition of a BGP inhibitory signal.

TABLE II

Allogeneic Mixed Lymphocyte Reaction

| Treatment | CPM |
| --- | --- |
| Medium | 16,330 ± 2,131 |
| mouse anti-human BGP (34B1) | |
| 1:125 | 41,246 ± 1,779 |
| 1:250 | 54,578 ± 2,437 |
| 1:500 | 34,987 ± 1,545 |
| 1:750 | 33,978 ± 1,036 |
| 1:1000 | 31,522 ± 1,087 |

TABLE II-continued

Allogeneic Mixed Lymphocyte Reaction

| Treatment | CPM |
| --- | --- |
| mouse anti-human BGP (5F4) | |
| 1:125 | 35,330 ± 1,615 |
| 1:250 | 33,191 ± 883 |
| 1:500 | 27,862 ± 2,635 |
| 1:750 | 23,511 ± 2,365 |
| 1:1000 | 38,826 ± 3,103 |
| Normal mouse serum (negative control) | |
| 1:125 | 18,491 ± 544 |
| 1:500 | 17,957 ± 772 |
| 1:1000 | 19,343 ± 471 |

Figure 8:
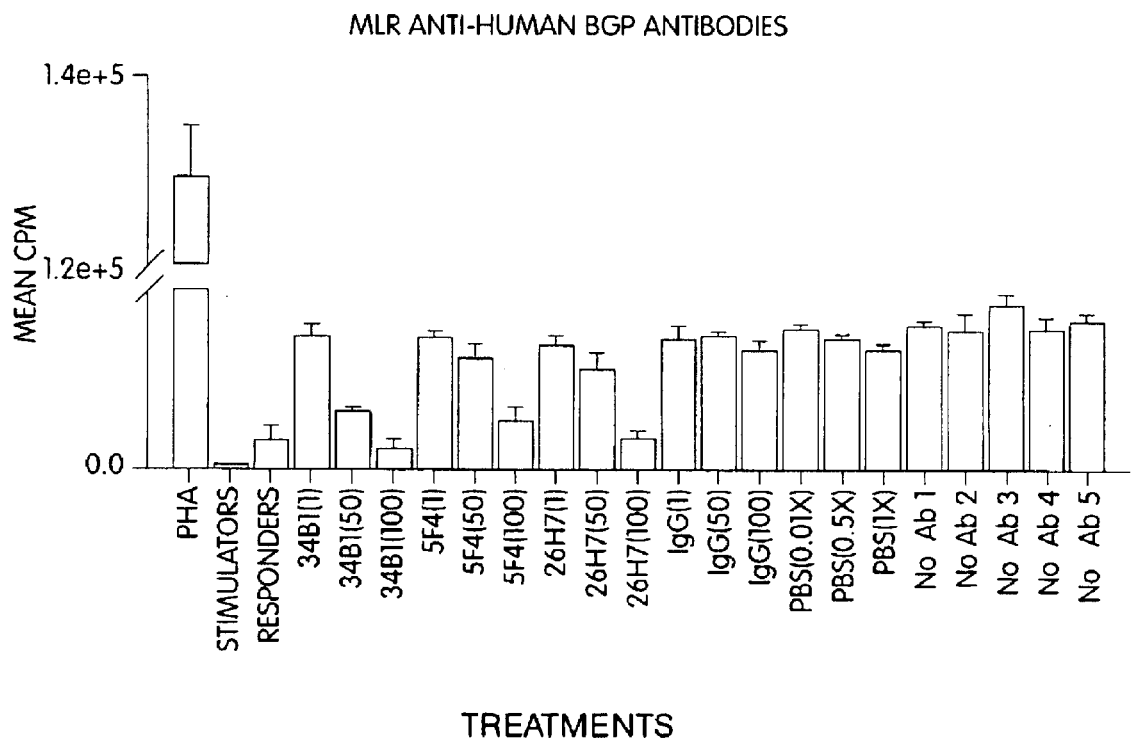
FIG. 8 shows inhibition of human allo-mixed lymphocyte reaction by anti-BGP monoclonal antibodies.

FIG. 8 shows the results of similar experiments. Stimulator (irradiated peripheral blood mononuclear cells) and responder (nonirradiated peripheral blood mononuclear cells) from two unrelated human study subjects were cocultivated in at $2 \times 10^5$ cells per well each in a 96-well flat bottomed plate in the presence or absence of either phytohemagglutinin-P (PHA; 1 $\mu$g/ml), irrelevant IgG1 at various concentrations (1–100 $\mu$g/ml) or the anti-CD66a specific monoclonal antibodies 34B1, 26H7 or 5F4 at various concentrations (1–100 $\mu$g/ml). After four days, 1 $\mu$Curie of $^3$H-thymidine was added per well for the last 18 hours of incubation and the plates harvested for assessment of proliferation. The y-axis shows the counts per minute. The S.E.M. is shown for each measurement.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference.

What is claimed is:

1. A method for suppressing specifically the cytotoxicity or proliferation of killer T cells in a subject, comprising:

administering to a subject in need of such treatment an agent that selectively increases cross-linking of biliary glycoprotein polypeptides, CD66a, on a killer T cell in an amount effective to suppress the activity of killer T cells in the subject, and wherein the agent is an antibody specific for said biliary glycoprotein or an antigen-binding fragment thereof that increases cross-linking of biliary glycoprotein on the killer T cell.

2. The method of claim 1, wherein the antibody is a monoclonal antibody.

3. The method of claim 1, wherein the antibody is a chimeric antibody or a humanized antibody.

4. The method of claim 1, wherein the antibody is a CD66a specific monoclonal antibody.

5. A method for suppressing specifically the cytotoxicity or proliferation of killer T cells in a subject, comprising:

administering to a subject in need of such treatment an agent that selectively increases cross-linking of biliary glycoprotein polypeptides, CD66a, on a killer T cell in an amount effective to suppress the activity of killer T cells in the subject, wherein the agent comprises an isolated ligand for the biliary glycoprotein polypeptide, wherein the ligand binds two or more biliary glycoprotein polypeptides on the killer T cell, and wherein the isolated ligand comprises a biliary glycoprotein polypeptide or fragment thereof.

6. The method of claim 5, wherein the fragment of biliary glycoprotein is selected from the group consisting of the N-terminal domain of CD66a, NA1B1 domain of CD66a, and the NA1B1A2 domain of CD66a.

7. The method of claim 5, wherein the biliary glycoprotein polypeptide or the fragment thereof is fused to an immunoglobulin molecule or a fragment thereof.

8. A method for suppressing specifically cytotoxicity or proliferation of killer T cells, comprising:

contacting a population of killer T cells with an agent that selectively increases cross-linking of biliary glycoprotein polypeptides, CD66a, on a killer T cell in an amount effective to suppress the cytotoxicity or proliferation of the killer T cells, and wherein the agent is an antibody specific for said biliary glycoprotein or an antigen-binding fragment thereof that increases cross-linking of biliary glycoprotein on the killer T cell.

9. The method of claim 8, wherein the antibody is a monoclonal antibody.

10. The method of claim 8, wherein the antibody is a chimeric antibody or a humanized antibody.

11. The method of claim 8, wherein the antibody is a CD66a specific monoclonal antibody.

12. A method for suppressing specifically cytotoxicity or proliferation of killer T cells, comprising:

contacting a population of killer T cells with an agent that selectively increases cross-linking of biliary glycoprotein polypeptides, CD66a, on a killer T cell in an amount effective to suppress the cytotoxicity or proliferation of the killer T cells, wherein the agent comprises an isolated ligand for the biliary glycoprotein polypeptide, wherein the isolated ligand binds two or more biliary glycoprotein polypeptides on the killer T cell, and wherein the isolated ligand comprises a soluble biliary glycoprotein molecule or a fragment thereof.

13. The method of claim 12, wherein the fragment of biliary glycoprotein is selected from the group consisting of the N-terminal domain of CD66a, NA1B1 domain of CD66a, and the NA1B1A2 domain of CD66a.

14. The method of claim 12, wherein the biliary glycoprotein polypeptide or the fragment thereof is fused to an immunoglobulin molecule or a fragment thereof.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Homo sapiens

<400> SEQUENCE: 1
caucaucauc auaagcttat ggggcacctc                                    30

<210> SEQ ID NO 2
<211> LENGTH: 30
<212> TYPE: DNA
<213> ORGANISM: Homo sapiens

<400> SEQUENCE: 2
gccattttct tggggcabct ccgggtatac                                    30

<210> SEQ ID NO 3
<211> LENGTH: 30
<212> TYPE: DNA
<213> ORGANISM: Homo sapiens
```

```
<400> SEQUENCE: 3
gtatacccgg agctgcccca agaaaatggc                                30

<210> SEQ ID NO 4
<211> LENGTH: 30
<212> TYPE: DNA
<213> ORGANISM: Homo sapiens

<400> SEQUENCE: 4
cuacuacuac uaagactatg aagttggttg                                30
```